US012599507B2

(12) United States Patent
Mazurkiewicz et al.

(10) Patent No.: US 12,599,507 B2
(45) Date of Patent: Apr. 14, 2026

(54) METHOD AND APPARATUS FOR MANUFACTURING AN ELASTIC LAMINATE AND A DISPOSABLE ABSORBENT HYGIENE PRODUCT COMPRISING THE ELASTIC LAMINATE

(71) Applicant: Essity Hygiene and Health Aktiebolag, Gothenburg (SE)

(72) Inventors: Tadeusz Mazurkiewicz, Brzeg (PL); Martien Vos, AR Zeist (NL)

(73) Assignee: ESSITY HYGIENE AND HEALTH AKTIEBOLAG, Gothenburg (SE)

( * ) Notice: Subject to any disclaimer, the term of this patent is extended or adjusted under 35 U.S.C. 154(b) by 126 days.

(21) Appl. No.: 18/258,831

(22) PCT Filed: Feb. 11, 2021

(86) PCT No.: PCT/SE2021/050107
§ 371 (c)(1),
(2) Date: Jun. 22, 2023

(87) PCT Pub. No.: WO2022/173338
PCT Pub. Date: Aug. 18, 2022

(65) Prior Publication Data
US 2024/0041663 A1     Feb. 8, 2024

(51) Int. Cl.
*A61F 13/15* (2006.01)
*B08B 5/02* (2006.01)

(52) U.S. Cl.
CPC .. *A61F 13/15699* (2013.01); *A61F 13/15747* (2013.01); *A61F 13/15764* (2013.01); *A61F 2013/1591* (2013.01); *B08B 5/026* (2013.01)

(58) Field of Classification Search
None
See application file for complete search history.

(56) References Cited

U.S. PATENT DOCUMENTS

| | | | |
|---|---|---|---|
| 6,235,137 | B1 | 5/2001 | Van et al. |
| 6,863,225 | B2 | 3/2005 | Nakamura |
| 6,905,081 | B2 | 6/2005 | Saidman et al. |

(Continued)

FOREIGN PATENT DOCUMENTS

| | | |
|---|---|---|
| CN | 103459047 A | 12/2013 |
| CN | 104869955 A | 8/2015 |

(Continued)

OTHER PUBLICATIONS

International Search Report (PCT/ISA/210) and Written Opinion (PCT/ISA/237) mailed on Sep. 29, 2021, by the Swedish Patent Office as the International Searching Authority for International Application No. PCT/SE2021/050107. (15 pages).

(Continued)

*Primary Examiner* — Barbara J Musser
(74) *Attorney, Agent, or Firm* — BUCHANAN INGERSOLL & ROONEY PC

(57) ABSTRACT

The present disclosure relates to a method of manufacturing an elastic laminate for an disposable absorbent hygiene product, said elastic laminate comprises at least a first continuous sheet and at least one elastic strand. Furthermore, it is disclosed an apparatus and a disposable absorbent hygiene product comprising an elastic laminate manufactured according to the method.

27 Claims, 14 Drawing Sheets

(56)    References Cited

U.S. PATENT DOCUMENTS

| | | | |
|---|---|---|---|
| 7,462,240 | B2 | 12/2008 | Harris et al. |
| 8,771,449 | B2 * | 7/2014 | Takino .............. A61F 13/15804 |
| | | | 156/204 |
| 10,046,352 | B2 | 8/2018 | Saine et al. |
| 2001/0022155 | A1 | 9/2001 | Nakamura |
| 2002/0083895 | A1 | 7/2002 | Nakamura et al. |
| 2003/0111162 | A1 | 6/2003 | Erdman |
| 2004/0164180 | A1 | 8/2004 | Harris et al. |
| 2015/0328056 | A1 | 11/2015 | Een et al. |

FOREIGN PATENT DOCUMENTS

| | | | |
|---|---|---|---|
| EP | 0170922 | A1 | 2/1986 |
| EP | 0235815 | A2 | 9/1987 |
| JP | S62276005 | A | 11/1987 |
| JP | 2016198576 | A | 12/2016 |
| WO | 0066351 | A3 | 11/2000 |
| WO | 0176772 | A3 | 10/2001 |

OTHER PUBLICATIONS

Office Action issued on Jul. 29, 2024, by the Japanese Patent Office in corresponding Japanese Patent Application No. 2023-548724, and an English Translation of the Office Action. (13 pages).

The extended European Search Report issued on Oct. 17, 2024, by the European Patent Office in corresponding European Application No. 21925954.6. (6 pages).

Office Action issued on Jan. 21, 2025, by the Japanese Patent Office in corresponding Japanese Patent Application No. 2023-548724, and an English Translation of the Office Action. (9 pages).

Office Action (Notification of the First Office Action) issued on Jul. 17, 2025, by the Chinese Patent Office in corresponding Chinese Patent Application No. 202180092301.X, and an English Translation of the Office Action. (27 pages).

Office Action (Decision of Rejection) issued on Feb. 2, 2026, by the Chinese Patent Office in corresponding Chinese Patent Application No. 202180092301, and an English Translation of the Office Action. (22 pages).

* cited by examiner

A - A

311

313          313

METHOD AND APPARATUS FOR MANUFACTURING AN ELASTIC LAMINATE AND A DISPOSABLE ABSORBENT HYGIENE PRODUCT COMPRISING THE ELASTIC LAMINATE

TECHNICAL FIELD

This disclosure relates to a method of manufacturing an elastic laminate for an absorbent article, the elastic laminate comprising at least a first continuous sheet and at least one elastic strand. The disclosure also relates to an apparatus and a product made according to the method.

BACKGROUND

Absorbent articles, such as diapers or incontinence guards, are articles which are worn adjacent the body, and used for the containment and absorption of bodily exudates, such as urine, blood, faeces and sweat. Such articles are usually supplied with elastic members, commonly in the form of one or more elastic strands. In the interests of manufacturing efficiency and economy, the elastic members are located in selected regions of the article, such as leg openings, waist openings, and standing gathers. Elastic members perform one or more functions, such as helping to maintain the article in place on the wearer, providing the article with a suitable three-dimensional form, and helping to seal portions of the article against the skin of the wearer, thus reducing the risk of leakage.

Absorbent articles are manufactured in high volumes, at high speeds. Methods are therefore required which allow the incorporation of elastic members e.g. in the form of one or more elastic threads or strands into or onto other components of an absorbent article during manufacture. Elastic members are usually only located in certain regions of the absorbent article, but are often supplied in continuous form (e.g. on a roll), so one or more steps of cutting the elastic members is usually required.

The elastic members are usually attached to the other components by liquid adhesive, such as hot melt adhesive. Various dispensing systems have been developed for applying hot melt adhesive onto the various components. In one example, hot melt adhesive is applied to one or more of thin elastic threads/strands and the threads/strands are then adhered to a flat nonwoven substrate to form an elasticized portion of the disposable absorbent personal hygiene product. Downstream of the dispensing system, the various components (e.g., flat substrate layers and elastic strands) usually pass through a pressure nip to secure the components together.

Over the last few years the desire for soft absorbent articles has increased, which is addressed by using softer materials. Those softer materials, however, generate dust and loose fibers during manufacturing, which may be problematic. Dust and loose fibers may cause issues in the gluing process for adding hot melt on the elastic strands. Issues include not enough glue being applied to the elastic strands and even breakage of the strands.

Some solutions have been proposed. One such solution is disclosed in US20040164180, which includes using a glue nozzle having an outlet through which air can flow. The outlet is directed towards the elastic strand and impinges the strand proximate to an upstream entrance to the notch of the nozzle. The air flow discharged from the outlet has a velocity or magnitude sufficient for overcoming the forces adhering the particulates to the strand and removing particulates from the strand either before, during, or after each particulate carried by strand enters the notch of the nozzle.

However, there is still a need for an alternative flexible solution.

SUMMARY

It is desired to provide an alternative flexible system which cleans elastic strands from dust and loose fibers or other contaminants before they are coated with adhesive.

In accordance with a first aspect of the present disclosure, there is provided a method of manufacturing an elastic laminate for a disposable absorbent hygiene product, said elastic laminate comprising at least a first continuous sheet and at least one elastic strand. The method comprises advancing said first continuous sheet having a first surface in a machine direction, and defining a width in a cross-machine direction;

advancing said at least one elastic strand in the machine direction in a stretched state;

dispensing a liquid adhesive onto said at least one elastic strand from a nozzle comprising at least one liquid discharge passage;

blowing air onto said at least one elastic strand from an air blowing device, said air blowing device being arranged at a predetermined distance upstream from said nozzle before said liquid adhesive is dispensed onto said at least one elastic strand in order to blow off dust, loose fibers or other contaminants.

By blowing air onto the elastic strand from an air blowing device arranged at a predetermined distance upstream from said nozzle before said liquid adhesive is dispensed onto said elastic strand, dust and loose fibers or other contaminants can be removed in an efficient way before the elastic strands enters the nozzle. This reduces the risk that not enough glue is applied to the elastic strands and also the breakage of the strands are reduced. It may be advantageous to have the air blowing device at a predetermined distance from the nozzle since the air used may not need to be heated in particular applications in which the air is applied at a predetermined distance from the nozzle and its liquid discharge passage. This may save costs since no heating device is needed to heat up the air in such example applications.

The first continuous sheet having a first surface in a machine direction and defining a width in a cross-machine direction may be a nonwoven material which may form a laminate together with the elastic strand in order to form for example a standing gather, a leg elastic and/or waist and/or belly elastic in an absorbent article. In the context of the present disclosure, a "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The first continuous sheet may advantageously be selected from, for example, of spunbond, air laid, wet laid, carded or meltblown nonwovens. The fibers may made of natural or synthetic materials, such as cellulosic fibres, regenerated cellulose, polyester fibres, polypropylene fibres, polyethylene fibres or the combination thereof or the like.

Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn).

Nonwoven fabrics can be formed by many processes such as meltblowing, spunbonding, solvent spinning, electrospinning, and carding.

The nonwoven material may be a laminate or a combination of several types of nonwoven materials, such as spunbond-meltblown or spunbond-meltblown-spunbond-type. The nonwoven material may be non elastic. The basis weight for the nonwoven layer can be varied of from 5 to 80 g/m2, for example from 10 to 40 g/m2, and specifically from 10 to 30 g/m2. When the basis weight is under 40 g/m2, sufficient breathability, drapeability and comfort for the product can be obtained. The basis weight of from 10 to 30 g/m2 has been found to provide enhanced comfort and flexibility to the wearer of the article while providing good processability.

The term "elastic strand" is intended to mean a thread or a strand which is made of elastic material, such as e.g. natural or synthetic rubber, thermoplastic elastomers, such as thermoplastic polyurethane or styrene block co-polymers or elastane, also referred as to spandex (polyurethane-polyurea copolymer). The elastic strand may be of the elastane type that is available under the trade name "LYCRA", but any suitable elastic strand may be used. The strand may have a linear mass density, dtex, of about 80-800 dtex.

The elastic strand is elongated during the production process. It may be elongated from about 30 to about 300% of the initial, non-tensioned original length, for example in the range of 70-250% and specifically in the range of 100-200% of the initial, non-tensioned original length. The elastic strand may be of a type that is able to tolerate an elongation of at least about 200% without breaking, so that it can be safely used in the production process without risk for breaking.

The liquid adhesives used for coating the strands may be hot melt adhesives, which have thermoplastic properties. Any type of known hot-melt adhesive may be used and the hot melt adhesive may be for example based on ethylene-vinyl-acetate (EVA), polyolefin, polyester and/or polyamide, polyurethane, styrene block copolymer, silicone rubber and/or natural soy protein based adhesives. The adhesive may be non-toxic. The adhesive may be a styrene block copolymer based hot-melt adhesive, such as a product similar to a product with a trademark Henkel Dispomelt 5482. Other examples of suitable hot-melt adhesives are produced for example by the company H. B. Fuller, for example products with the product name NW1002 or FC8200, and Bostic H4281. The nozzle is an adhesive nozzle. The nozzle and the air blowing device have the same features and advantages as described in relation to the apparatus, which will be described further below.

In one example embodiment said method may also comprise joining said at least one elastic strand to said first surface of said first continuous sheet after said liquid adhesive is dispensed from said liquid discharge passage onto said elastic strand.

In one example embodiment said air blowing device is a separate device from said nozzle. By having the air blowing device as a separate device existing manufacturing machines and/or lines, can be supplemented. Hence, existing equipment/manufacturing lines may be easily supplemented with the air blowing device. The air blowing device can be used on any machine or production line and is not dependent on a specific supplier of the machines or the supplier of the nozzle equipment. Further, having a separate air blowing device provides flexibility for adjusting the location of that device, as well as adjusting the angle of application of the air relative to the elastic strand.

In one example embodiment said air blowing device comprises at least one air discharge passage for blowing said air onto said at least one elastic strand via said air discharge passage, said at least one air discharge passage comprises a first imaginary centre axis which in its extension intersects with said at least one elastic strand at a first point and said at least one liquid discharge passage of said nozzle comprises a second imaginary centre axis which in its extension intersects with said at least one elastic strand at a second point; and said predetermined distance is between said first point and said second point along said at least one elastic strand and said predetermined distance is between about 150 mm and about 900 mm, specifically between about 150 mm and about 600 mm. If for example air is used which is not heated by for example an air heating device, the air blowing device may not be arranged too close to the nozzle since the unheated air might cool the nozzle and the adhesive to be distributed on the elastic strand. This may result in bad quality of the adhesive bonding in the laminate and influence the quality of the disposable absorbent hygiene product.

In one example embodiment said method further comprises guiding the at least one elastic strand to the nozzle with an elastic strand guide and said elastic strand guide is arranged between said nozzle and said air blowing device. The elastic strand guide guides the at least one elastic strand in a desired position within the machine. The elastic strand guide may be a guiding roll comprising grooves on its outer circumferential area. Each elastic strand is arranged in a respective groove. The roll may rotate. The elastic strand guide may also be several guide rolls connected together and which rotate independently of each other, with each guide roll having one or more grooves for the elastic strand to be arranged in.

In one example embodiment said elastic strand guide is arranged closer to said air blowing device than to said nozzle.

In one example embodiment said air blowing device blows air onto said elastic strand guide and onto said at least one elastic strand. This way any dust and/or loose fibres which may be on the elastic strand and on the elastic strand guide may be simultaneously cleaned. This improves the manufacturing even further.

In one example embodiment said air blowing device blows cold air onto said at least one elastic strand. With cold air it is meant not heated air. That is, the air has not been intentionally heated by a heating device.

In one example embodiment said air blowing device comprises at least one air discharge passage for blowing said air onto said at least one elastic strand via said air discharge passage.

In one example embodiment said air blowing device blows air with an air pressure in the range of about 0.5-1.5 bar, specifically in the range of 1-1.5 bar. Hence, the air coming out from each air discharge passage has an air pressure in the range of 0.5-1.5 bar, specifically in the range of 1-1.5 bar. This gives the air discharged from the respective air discharge passage a velocity or magnitude sufficient for overcoming the forces adhering the particulates to the strand and removing particulates from the strand.

In one example embodiment said air blowing devices comprises at least one air discharge passage for blowing said air onto said at least one elastic strand via said at least one air discharge passage and said at least one air discharge passage is arranged above or under said at least one elastic strand at a predetermined distance in order to blow air onto said at least one elastic strand. The at least one air discharge passage comprises a first imaginary centre axis which in its extension intersects with said at least one elastic strand at a first point and said predetermined distance is to be measured from said at least one air discharge passage and said first point along said first imaginary centre axis.

In one example embodiment the predetermined distance between said at least one air discharge passage and said at least one elastic strand is in the range of 30-70 mm. It may for example be 40 mm. The advantage of having the air discharge passage close to the elastic strand is that less air energy (bar) is needed to blow the dust away. This also reduces the risk of undesired air flow in the surrounding of the air blowing device, which in a worst-case scenario can disturb other parts of the manufacturing line.

In one example embodiment said air blowing device comprises at least one air discharge passage for blowing said air onto said at least one elastic strand via said at least one air discharge passage, said at least one air discharge passage comprises a first imaginary centre axis which in its extension intersects with said at least one elastic strand at a first point, said first imaginary centre axis is in an angle to said at least one elastic strand and said angle is in the range between about 50°-130°, specifically 70°-110°. By distributing the air at an angle relative to the elastic strand it increases the chances that all dust and loose fibers or other contaminants are removed even further.

In one example embodiment said method further comprises folding the first continuous sheet to form a first layer fold, and joining the first continuous sheet and the first layer fold, wherein the first layer fold overlaps said at least one elastic strand. By folding the first continuous sheet to form a first layer fold which overlaps with the elastic strand a standing gather can be formed for an absorbent article. Alternatively, that construction may form a leg elastic or a waist elastic.

The edges in the crotch region in the leg area can be provided with leg elastics arranged substantially in the longitudinal direction of the article. Leg elastics can be used in order to improve the fit and provide an extra leakage barrier of the disposable wearable absorbent article.

Standing gathers extend upwardly generally about respective side edges of the absorption body at the side of the topsheet. Standing gathers define barriers or walls at the respective side edges of a central crotch area of the absorbent article, and act to prevent or retard lateral flow of body fluidic material such as urine or fluidic fecal material. The standing gathers may run substantially parallel to the longitudinal edges at the crotch region in a longitudinal direction of the absorbent article. The standing gathers contain elastics strands and may be elastically gathered at least in their centre portions, which provide means for a good fit so as to prevent any leakage. The standing gathers may extend in the longitudinal direction over the entire length of the absorbent product. It will be appreciated, however, that, the standing gathers may be shorter.

The purpose of the waist elastic is to provide the absorbent article with a good fit around the waist of the wearer wearing the article. The waist elastic is fastened relatively close to the waist edges around the waist opening.

In one example embodiment said method further comprises advancing a second continuous sheet having a first surface in the machine direction, and defining a width in a cross-machine direction, joining said at least one elastic strand between said first surface of said first continuous sheet and said first surface of said second continuous sheet after said liquid adhesive is dispensed from said liquid discharge passage onto said elastic strand. By having the elastic strand arranged between two continuous sheets front or back elastics in an open diaper can be manufactured or leg elastics. Alternatively, a front and/or a back waist panel of a pant diaper with waist elastics and belly elastic can manufactured. The second continuous sheet may be a nonwoven material which may form a laminate to be used as, for example, a standing gather, leg elastic and/or waist and/or belly elastic in an absorbent article. The definition of a nonwoven material is the same as for the first continuous sheet.

The various nonwoven material layers of the elastic laminate may be of the same or different materials and may have the same, similar or different basis weights. If different materials are selected, an elasticised laminate is attainable having different surface characteristics across the sheet. For example, the layers may have different friction properties or different liquid/vapour permeability properties According to another aspect of the present disclosure, there is provided an apparatus for manufacturing an elastic laminate for a disposable absorbent hygiene product. Said elastic laminate comprises at least a first continuous sheet and at least one elastic strand. Said apparatus comprising:

a first feeding device configured to continuously advancing said first continuous sheet having a first surface in a machine direction, and defining a width in a cross-machine direction;

a second feeding device configured to continuously advancing at least one elastic strand in the machine direction in a stretched state;

a nozzle having at least one liquid discharge passage to dispense a liquid adhesive onto said at least one elastic strand;

an air blowing device arranged at a predetermined distance upstream from said nozzle so that said air blowing device blows air onto said at least one elastic strand before said liquid adhesive is dispensed onto said at least one elastic strand.

The apparatus has the same advantages described above in connection with the method and the definitions provided above for, for example, the first continuous sheet, the at least on elastic strand and the liquid adhesive apply also to the apparatus herein described. The features, the definitions and the advantages described below in connection with the apparatus, also applies for the method.

The first feeding device may be in the form of rollers which feed the first continuous sheet. The second feeding device may also be in the form of rollers which feed the at least one elastic strand. Further, a tension control device may be used to create the needed elastic tension of the elastic strand.

The air blowing device is a device which blows air onto the elastic strands in order to remove dust, loose fibers, and other contaminants that may be found in a manufacturing environment. The air blowing device may comprise one or several air blowing heads which are connected to a pressurized air source. Each air blowing head may comprise one or more air discharge passages through which the pressurized air will pass. The air discharge passages are directed towards the elastic strands. The number of air discharge passage may be the same as the number of elastic strands which are going to be cleaned and the distances between the air discharge passages may be the same as the distances between the elastic strands to be cleaned. The air blowing device may for example be an air knife from Silvent AB of Boras, Sweden or a device with one or several air nozzles connected together to form the air blowing device. An example of an air nozzle which could be used is the AIR NOZZLE SILVENT 9002W-S from Silvent AB. However, the air blowing device is not limited to be an air knife or a device with one or several air nozzles connected together from the company Silvent AB. Any other suitable air blowing device can be used in order to remove contaminants such as dust and loose fibers from the elastic strands.

The nozzle having at least one liquid discharge passage is a glue nozzle, i.e. an adhesive nozzle. The nozzle may be a nozzle of contact dispensing system. Such a system is a slot coating nozzle including one or more grooves configured to be filled with extruded adhesive. Each individual strand is coated separately, by the slot coating device which can be for example a V-slot or comb-slot-coating device. By the comb-slot or comb-coater is meant in this case a slot coater that is prepared with a shim that is designed in such way that it can be used as guiding device for the elastic strands. However, the device can also be a slot coater that is V-notched for each strand and with and without guiding device attached. The adhesive may be arranged as discrete bonding points on the elastic strand or alternative fully cover the elastic strand.

In one example embodiment said apparatus may further comprise a joining device configured to join said at least one elastic strand to said first surface of said first continuous sheet after said liquid adhesive is dispensed from said liquid discharge passage onto said at least one elastic strand. The joining device is configured to join said at least one elastic strand to said first surface of said first continuous sheet may take the form of two rolls positioned relative to one another to define a pressure nip that secures the components together when they pass between the two rolls. Alternatively, the joining device may be one roll and a contra rolling surface which forms the pressure nip.

In one example embodiment said air blowing device is a separate device. By having the air blowing device as a separate device existing manufacturing machines and/or lines, can be supplemented. Hence, existing equipment/manufacturing lines may be easily supplemented with the air blowing device. The air blowing device can be used on any machines and is not dependent on a specific supplier of the machines or the supplier of the nozzle equipment. Further, having a separate air blowing device makes it easy to adjust the placement of that device in the machine as well as the angle of application of the air relative to the elastic strand In one example embodiment said air blowing device comprises at least one air discharge passage for blowing said air onto said at least one elastic strand via said air discharge passage, said at least one air discharge passage comprises a first imaginary centre axis which in its extension intersects with said at least one elastic strand at a first point and said at least one liquid discharge passage of said nozzle comprises a second imaginary centre axis which in its extension intersects with said at least one elastic strand at a second point; and said predetermined distance is between said first point and said second point along said at least one elastic strand and said predetermined distance is between about 150 mm and about 900 mm, specifically between 150 mm and 600 mm. If for example air is used which is not heated by an air heating device the air blowing device may not be arranged too close to the nozzle since the relatively cool air may undesirably cool the nozzle and/or the adhesive to be distributed onto the elastic strand.

This inadvertent effect may result in bad quality of the adhesive bonding in the laminate and influence the quality of the disposable absorbent hygiene product being made.

In one example embodiment said apparatus further comprises an elastic strand guide arranged to guide the at least one elastic strand to the nozzle and said elastic strand guide is arranged between said nozzle and said air blowing device. The elastic strand guide guides the at least one elastic strand in a desired position within the apparatus. The elastic strand guide may be in the form of a guiding roll comprising grooves on its outer circumferential area. Each elastic strand is arranged in a respective groove. The roll may rotate. The elastic strand guide may alternatively be in the form of several guide rolls connected together and which rotate independently of each other. Each guide roll has one or more grooves for the elastic strand to be arranged in.

In one example embodiment said elastic strand guide is arranged closer to said air blowing device than to said nozzle.

In one example embodiment said air blowing device blows air onto said elastic strand guide and onto said at least one elastic strand. This way any dust, loose fibres, and/or other contaminants may be simultaneously cleaned off the surface of the elastic strand. This improves the manufacturing even further.

In one example embodiment said air blowing device blows cold air onto said at least one elastic strand. By cold air it is meant air that has not been intentionally heated by a heating device.

In one example embodiment said air blowing device comprises at least one air discharge passage for blowing said air onto said at least one elastic strand via said air discharge passage.

In one example embodiment said air blowing device blows air with an air pressure in the range of 0.5-1.5 bar, specifically in the range of 1-1.5 bar. Hence, the air coming out from each at least one air discharge passage is with an air pressure in the range of 0.5-1.5 bar, specifically in the range of 1-1.5 bar. This gives the air discharged from the air discharge passage a velocity having a magnitude sufficient for overcoming the forces adhering the particulates to the strand and removing particulates from strand.

In one example embodiment said air blowing devices comprises at least one air discharge passage for blowing said air onto said at least one elastic strand via said at least one air discharge passage and said at least one air discharge passage is arranged above or under said at least one elastic strand at a predetermined distance. The at least one air discharge passage comprises a first imaginary centre axis which in its extension intersects with said at least one elastic strand at a first point and said predetermined distance is to be measured from said at least one air discharge passage and said first point along said first imaginary centre axis.

In one example embodiment said predetermined distance between said air discharge passage and said at least one elastic strand is in the range of 30-70 mm. It may for example be 40 mm.

In one example embodiment said air blowing device comprises at least one air discharge passage for blowing said air onto said at least one elastic strand via said air discharge passage, said at least one air discharge passage comprises a first imaginary centre axis which in its extension intersects with said at least one elastic strand at a first point, said first imaginary centre axis is in an angle to said at least one elastic strand and said angle is in the range between about 50°-130°, specifically 70°-110° Distributing the air at an angle relative to the elastic strand it increases the chances that all dust, loose fibers, and/or other contaminants are fully removed from the surface of the elastic strand.

In one example embodiment said air blowing device comprises at least one air discharge passage, and each of said at least one air discharge passage blows air onto a respective elastic strand. This way, it is ensured that each elastic strand is being cleaned before it arrives to the nozzle.

In one example embodiment said apparatus further comprises a folding device folding the first continuous sheet to form a first layer fold, and directly joining the first continuous sheet and the first layer fold, wherein the first layer fold overlaps said at least one elastic strand. By folding the first continuous sheet to form a first layer fold which overlaps with the elastic strand a standing gather is formed for an absorbent article. Alternatively, that construction may form a leg elastic or a waist elastic, for example.

In one example embodiment said apparatus further comprises a third feeding device configured to continuously advance a second continuous sheet having a first surface in a machine direction, and defining a width in a cross-machine direction, and a joining device to join said at least one elastic strand between said first surface of said first continuous sheet and said first surface of said second continuous sheet after said liquid adhesive is dispensed from said liquid discharge passage onto said elastic strand. By having the elastic strand arranged between two continuous sheets, front or back elastics in an open diaper can be manufactured, or alternatively leg elastics. Alternatively, a front and/or a rear waist panel of a pant diaper with waist elastics and belly elastic can manufactured. The second continuous sheet may be a nonwoven material. The definition of a nonwoven material is the same as for the first continuous sheet. The third feeding device may be a roller or any other kind of device suitable to feed the second continuous sheet.

According to another aspect of the present disclosure, there is provided a disposable absorbent hygiene product comprising an elastic laminate manufactured according to the method described above. The disposable absorbent hygiene product which also may be called disposable absorbent hygiene article, absorbent product or absorbent article, may be a pant-type absorbent article, i.e. a pant diaper, all-in-one absorbent article i.e. an open diaper, a belt type absorbent article, i.e. a belted diaper also called belt diaper or an absorbent pad.

Generally, all terms used throughout this disclosure are to be interpreted according to their ordinary meaning in the technical field, unless explicitly defined otherwise herein. All references to "a/an/the [element, device, component, means, step, etc]" are to be interpreted openly as referring to at least one instance of that element, device, component, means, step, etc., unless explicitly stated otherwise.

Other objectives, features and advantages of the example embodiments of the present disclosure will appear from the following detailed disclosure, as well as from the drawings. The skilled person will readily realize that different features of the example embodiments may be combined to create embodiments other than those expressly described in the following, without departing from the scope of the present disclosure.

BRIEF DESCRIPTION OF THE DRAWINGS

The above, as well as additional objects, features and advantages of the present disclosure, will be better understood through the following illustrative and non-limiting detailed description of example embodiments of the present invention, with reference to the appended drawings, where the same reference numerals will be used for similar elements, wherein:

FIG. 7c shows an enlarged view of the air blowing device and the nozzle in FIG. 7a.

Figure 1:
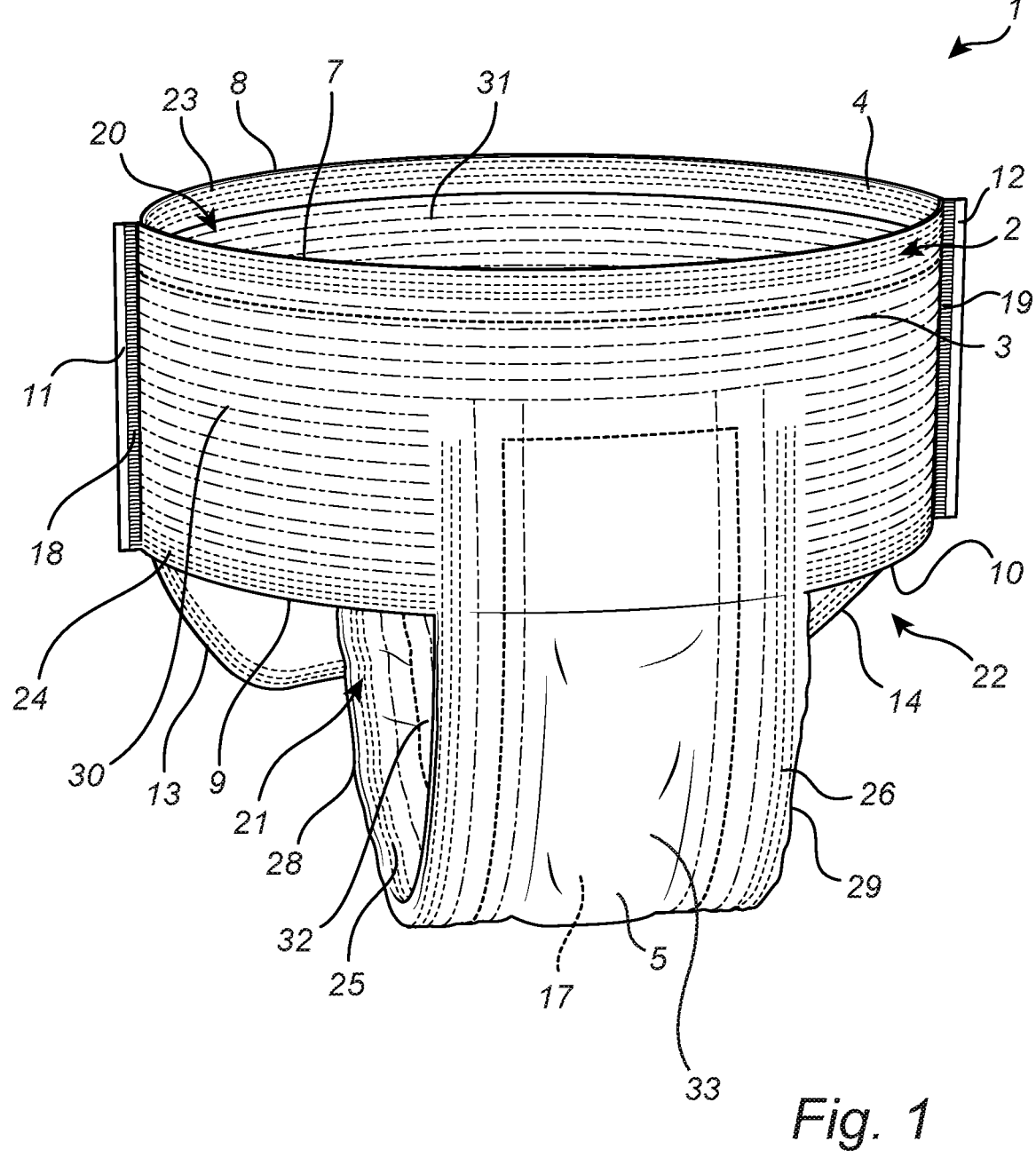
FIG. 1 schematically shows a perspective front view of a pant-type absorbent article, i.e. a pant diaper.

All the figures are highly schematic, not necessarily to scale, and they show only parts which are necessary in order to elucidate the invention, other parts being omitted or merely suggested.

DETAILED DESCRIPTION

Various aspects of the disclosure will now be described more fully hereinafter with reference to the accompanying drawings, in which example embodiments are shown. The example embodiments may, however, take many different forms and should not be construed as limited to the details of embodiment set forth herein; rather, these embodiments are provided for thoroughness and completeness. Like reference characters refer to similar elements throughout the description.

For purposes of description herein the terms "rear," "front,", "longitudinal,", "inner," "outer,", "exterior," and derivatives thereof relate to the example embodiments as oriented in the figures. However, it is to be understood that the example embodiments may assume various alternative orientations, except where expressly specified otherwise. It is also to be understood that the examples illustrated in the figures and described herein are simply example embodiments. Hence, dimensions and other physical characteristics relating to the example embodiments disclosed herein are not to be considered as limiting, unless expressly stated otherwise.

The disclosure mainly refers to disposable absorbent hygiene products, which means products that are not intended to be laundered or otherwise restored or reused as absorbent products after use. By "absorbent product" is meant a product that absorbs or is adapted to absorb bodily fluids, such as urine and/or blood, and/or contain solid excrements.

Absorbent articles/products, such as diapers or incontinence guards, are articles which are worn adjacent the body, and used for the containment and absorption of bodily exudates, such as urine, blood, faeces and sweat. The absorbent hygiene product, also called absorbent article, according to the present disclosure is a disposable product. The term "disposable" is used to describe absorbent products which generally are not intended to be laundered or otherwise restored, or reused as an absorbent product, e.g., they are intended, to be discarded after a single use and may also be configured to be recycled, composted or otherwise disposed of in an environmentally compatible manner.

"Absorbent articles/products" also called disposable absorbent hygiene product or article refer to consumer products which absorb and contain body exudates, and more specifically, refers to products which are placed against or in proximity to the body of the wearer to absorb and contain the various exudates discharged from the body. Absorbent articles, also called absorbent hygiene products, comprise, for example, diapers and incontinence devices. Diapers comprise for example all-in-one diapers, pant diapers and belted diapers. The diapers can be diapers for babies, young children or adults.

Such articles are usually supplied with elastic members, commonly in the form of one or more elastic strands. The elastic members are located in selected regions of the article, such as leg openings, waist openings, and standing gathers. Elastic members may have a number of functions. For example, they may help to maintain the article in place on the wearer, provide the article with a suitable three-dimensional form, and/or help to seal portions of the article against the skin of the wearer, thus reducing the risk of leakage.

So-called all-in-one diapers, also called open diapers are characterized in that they include fastening tabs/panels with which the front and rear portion of the diaper are joined when the diaper is applied around the waist of a wearer. All-in-one diapers may have elastics in the front and/or the rear region. They usually also have leg elastics and may also be provided with standing gathers.

So-called pant diapers are characterized in that the front and rear portion of the diaper are joined at the waist. This type of diaper is intended to be put on a wearer precisely like a pair of underpants, i.e. drawn over the wearer's legs. The joining at the waist part of the pant diapers can usually be broken open to remove the pant diapers from the wearer so that is not required to pull the pants down over the wearer's legs and feet to remove the pant diaper. Pant diapers normally comprise both elastic areas in the waist section and around the leg openings. Pant diapers that can be opened and reclosed by means of refastening means also exist. Such pant diapers can be opened for example to check whether the product has been soiled or in order to adjust the width of the product and then reclosed afterwards. Pants diapers usually have elastics both in the front and the rear waist panel in the waist region and in the belly region. There may, however, be that only the front or the rear region comprise elastics in the waist and/or belly region. Pants diapers are also usually provided with leg elastics and may also be provided with standing gathers.

So-called belt diapers/belted products are characterized in that they comprise a belt that is transversely oriented in relation to the chassis of the diaper and which is attached integrally with a chassis. An absorption body is arranged in the chassis. The belt may have two belt portions extending on either side of the rear end or the front end of the chassis. When putting on a belt diaper, the two belt portions are intended to be fastened around the waist of the wearer in a first stage. The front end or the rear end of the chassis of the belted diaper is hanging loose from the belt between the legs of the wearer. Once the belt portions have been joined together, the absorbent chassis is led between the wearer's legs and fastened to the belt. The belt comprises fixing surfaces intended to stick to a fixing element arranged on the chassis of the diaper by its free transverse edge. This type of product is particularly useful for caregivers who care for patients that may have dementia or the like. Another type of belt diaper is in the form of a two-piece product that comprises a separate belt and a separate chassis with an absorbent structure. When in use the belt is fastened around the wearer's waist, following which the chassis is joined to the outside of the belt by means of hook and loop elements or tape elements in the corners of the chassis.

Belted diapers may have elastics in the front and/or the back waist region. They are usually also provided with leg elastics and may also have standing gathers.

As mentioned above all three of the diaper types described above may have leg elastics. Leg elastics can be used in order to improve the fit and provide an extra leakage barrier of the disposable wearable absorbent product. The edges in the crotch region in the leg area can be provided with leg elastic arranged substantially in the longitudinal direction of the product. The task of the leg elastics includes improving the fit of the product. The respective leg elastic can consist of one or more elastic strands that in the extended state have been joined to at least one of the layers in the area of the crotch region by gluing, ultrasonic welding or the like. Alternatively, the respective leg elastic can consist of elastic ribbon material of foamed material, for example.

The respective leg elastic is preferably arranged on the side of the backsheet that is intended to face away from the wearer when in use.

All three diaper types described above may also have a pair of standing gathers, which extend upwardly generally about respective side edges of the absorption body at the side of the topsheet. Such a standing gather defines a barrier or wall at the respective side edge of a central crotch area of the absorbent product, which acts to prevent or retard lateral flow of body fluidic material such as urine or fluidic fecal material. The standing gathers may run substantially parallel to the longitudinal edges at the crotch region in a longitudinal direction of the absorbent product. The standing gathers may contain elastics and may include an elastic material, such as an elastic strand, yarn or ribbon material, and may be elastically gathered at least in their centre portions, which provide means for a good fit so as to prevent any leakage. The standing gathers may extend in the longitudinal direction L over the entire length of the absorbent product. It will be appreciated, however, that, the standing gathers may be shorter.

All three diaper types described above may have waist elastic. Waist elastic includes at least one elastic material, such as an elastic strand, yarn or ribbon material which is fastened to the chassis at least partly along the waist edges forming part of the front portion and/or the rear portion. The purpose of the waist elastic is to provide the absorbent product with a good fit around the waist of the person wearing the article. The waist elastic is fastened relatively close to the waist edges around the waist opening.

Further elastic materials may be arranged adjacent to the waist elastic in the region of the belly, i.e. also called belly elastics, and the backside of the wearer, i.e. in a direction towards the crotch. The purpose of these elastic components is to contribute to a good fit and comfort for the wearer of the article. These are usually present in the so called pant diapers.

Other products where elastics can be used may for example be a disposal absorbent pad which can be placed in a wearer's underwear. The disposal absorbent pad can be provided with leg elastics or standing gathers in a similar way as the three kind of diapers described herein. Hence, such a disposable absorbent pad will not be further described.

FIG. 1 shows an embodiment of a disposable pant-type absorbent article 1 illustrated in an assembled and ready-to-use state. The same absorbent article 1 is also shown in FIG. 2, but in a condition in which it is laid out flat and as viewed from above in order to show its main components.

Figure 2:
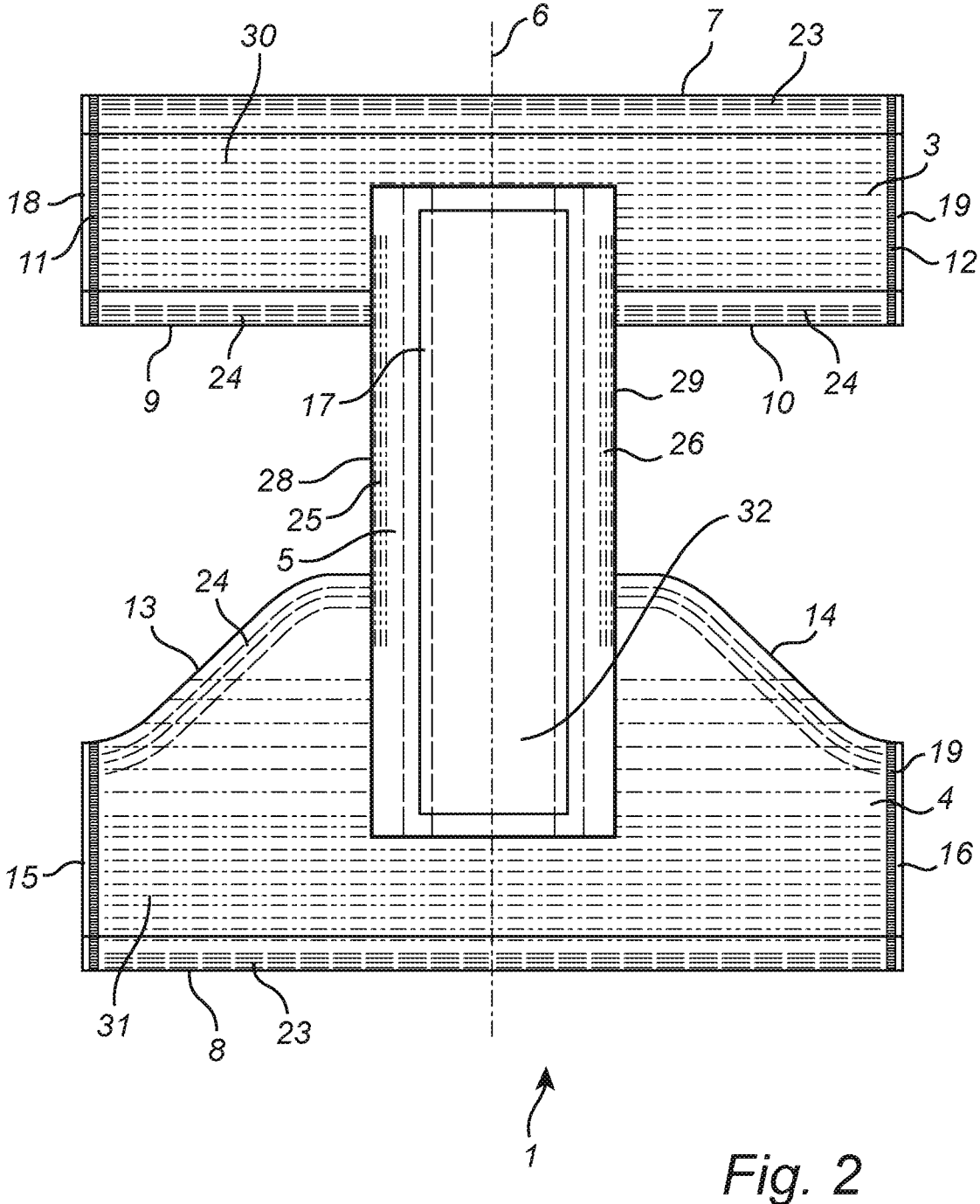
FIG. 2 shows a top view of the pant-type absorbent article in FIG. 1.

With reference to FIG. 1 and FIG. 2, the pant-type absorbent article 1 is for example in the form of a pant diaper, a sanitary pant or an incontinence pant adapted for use by a baby, child or adult, male or female wearer. The pant-type absorbent article 1 according to FIG. 1 comprises a single-piece chassis 2 having a front portion 3, a back portion 4, also called rear portion 4, a crotch portion 5 connecting the front and back portions 3, 4, and a centre line 6 (see FIG. 2) in the longitudinal direction of the article. The absorbent article 1 has a longitudinal direction, a transverse direction and a thickness direction.

The front portion 3 has a waist edge 7, a pair of leg edges 9, 10 and a pair of side edges 11, 12. Furthermore, the back portion 4 has a waist edge 8, a pair of leg edges 13, 14 and a pair of side edges 15, 16.

As mentioned above, the absorbent article 1 comprises a crotch portion 5, which comprises an absorption body 17 located mainly in said crotch portion 5. The absorption body 17 may be manufactured separately from the chassis 2 and inserted and fastened to the chassis 2 at a suitable manufacturing step.

The side edges 11, 12 of the front portion 3 are attached to the opposite side edges 15, 16 of the back portion 4 by means of permanent or re-closable side connections 18, 19 such as side seams, hook and loop fasteners, adhesive fasteners, or the like, in order to at least partly define a waist opening 20 and a pair of leg openings 21, 22.

A first elastic element in the form of an elastic waist component 23 is fastened to the chassis 2 at least partly along the waist edges 7, 8 forming part of the front portion 3 and the back portion 4 respectively. The purpose of the elastic waist component 23 is to provide the absorbent article 1 with a good fit around the waist of the person wearing the article. The elastic waist component 23 is fastened relatively close to the waist edges 7, 8, around the waist opening 20.

Furthermore, a second elastic element in the form of an elastic leg component 24 is fastened to the chassis 2 at least partly along the leg edges 9, 10 of the front portion 2 for the purpose of providing the absorbent article 1 with a good fitting around the legs of the wearer wearing the article. The elastic leg component 24 is fastened relatively close to the leg edges 9, 10.

As shown in particular in FIG. 2, the elastic leg component 24 forms a straight line in the front portion 3 and has a curved configuration in the back portion 4.

Furthermore, a first absorbent body elastic 25 and a second absorbent body elastic 26 are arranged along the crotch portion 5. The first absorbent body elastic 25 is arranged along a first crotch edge 28 whereas the second absorbent body elastic 26 is arranged along a second crotch edge 29. In particular, the first absorbent body elastic 25 and the second absorbent body elastic 26 are arranged relatively close to the longitudinal crotch edges 28, 29 and forms a second set of leg elastics. In a similar manner, the elastic waist component 23 and the elastic leg component 24 are also arranged relatively close to the waist edges 7, 8 and the leg edges 9, 10, respectively, as shown in FIG. 1 and FIG. 2.

If the elastic leg component 24 and the elastic waist component 23 are fastened at a location close to the leg and waist edges 7, 8, 9, 10, respectively, less non-elasticised web material is available at the leg and waist edges such that less frillings is created along said edges. This may be desirable, since a large amount of material at the leg edges may be perceived as uncomfortable by a wearer and may give the wearer an impression that the article is not similar to conventional underwear.

Having the elastic leg component 24 positioned closer to the leg edge 9, 10 may also result in an absorbent article 1 having an improved fit which corresponds to the shape of the legs of the wearer.

Furthermore, as shown in FIG. 1 and FIG. 2, the absorbent article 1 comprises a front elastic component 30 and a back elastic component 31 which are both based on a number of elastic strands mounted at a certain distance from each other in a generally parallel manner around the article 1, i.e. the region of the belly and the backside of the wearer. The purpose of these elastic components 30, 31 is to contribute to a good fit and comfort for the wearer of the article 1. In particular, the configuration of the elastic strands can be adapted to the male and female anatomy and the need for a suitable fit and comfort for male and female wearers of the article 1.

These elastic components are normally provided with a number of elastic strands, also called elastic threads, which are arranged along a waist edge, a leg edge and two crotch edges.

The positioning of the elastic strands and also the elastic properties of the elastic strands can be individually adapted so as to provide a configuration of the back elastic component 31 and front elastic component 30 which may be arranged so as to individually fit the male and female anatomy, respectively. More precisely, the positioning of the elastic strands refers to the manner in which the strands are laid out, in a geometric sense, along the absorbent articles in the array and also the distance between any two adjacent elastic strands.

The absorbent article 1 comprises a liquid permeable topsheet 32, i.e. a sheet which is intended to face the wearer of the article 1, and a liquid impermeable backsheet 33, i.e. a sheet which is placed so as to face the garment worn by the wearer.

The absorption body 17 is arranged between the topsheet 32 and the backsheet 33.

The topsheet 32 and backsheet 33 may be connected to each other for example by adhesive bonding, gluing or welding by heat or ultrasonic for example. The topsheet 32 and/or the backsheet 33 may further be attached to the absorbent body by any method known, such as adhesive or heat-bonding.

The pant-type absorbent article 1 may also have standing gathers (not shown).

Figure 3:
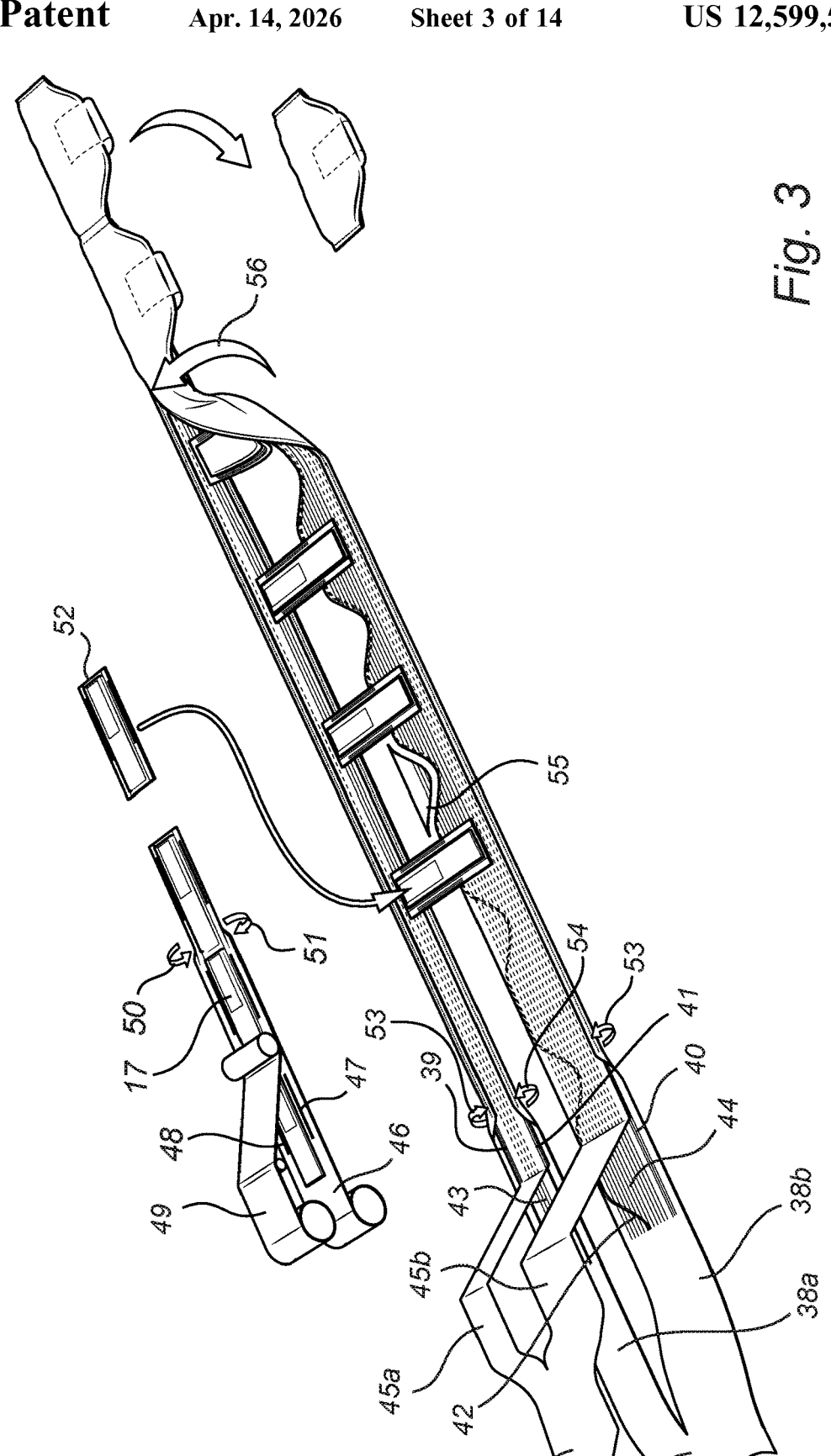
FIG. 3 shows a schematic illustration of a manufacturing process for pant-type absorbent article in FIGS. 1 and 2.

An example embodiment of a manufacturing line for a pant-type absorbent article 1 is schematically illustrated in FIG. 3. A first continuous sheet 38 of web material is supplied and is also divided, in a lengthwise manner, so as to form a first web section 38*a* and a second web section 38*b*. The first web section 38*a* forms the basis of a backsheet for the front portion 3 (see FIGS. 1a and 2) of the absorbent article 1, whereas the second web section 38b forms the basis of a backsheet for the back portion 4. Alternatively, the first web section 38a and the second web section 38b are two separate webs.

A plurality of strips of elastic material are attached to the first and second web sections 38a, 38b in a tensioned state. More precisely, a first strip 39 and a second strip 40 of elastic material form the basis of the elastic waist component 23, and a third strip 41 and a fourth strip 42 of elastic material form the basis of the elastic leg component 24. Also, a fifth strip 43 and a sixth strip 44 of elastic material form the basis of the front elastic component 30 and the back elastic component 31, respectively.

The strips 39, 40, 41, 42, 43, 44 of elastic material are glued to the continuous sheets 38a, 38b of web material, and said strips are intended to form an elastic laminate, i.e. an elastic web feature of the absorbent article 1 as described above with reference to FIGS. 1 and 2. Alternatives to gluing is ultrasonic bonding, welding, embossing, mechanical fastening, or the like.

The method and the apparatus for forming the elastic laminate is shown and described in FIGS. 7a-9.

Next, a further continuous sheet 45 of web material, i.e. a second continuous sheet, is provided and is split longitudinally in order to form a third web section 45a and a fourth web section 45b. The third web sections 45a forms the basis of a topsheet for the front portion 3 whereas the fourth web section 45b forms the basis of a topsheet for the back section 4. Alternatively, the third web section 45a and the fourth web section 45b are separate webs.

The third web section 45a and the fourth web section 45b are joined to the first web section 38a and the second web section 38b, respectively, in order to form a laminated product having the strips 39, 40, 41, 42, 43, 44 of elastic material sandwiched between the first web section 38a and the third web section 45a, and also between the second web section 38b and the fourth web section 45b. The attachment of the above-mentioned web sections and elastic strips is here described as being performed in consecutive steps or they may be performed in a single step.

Figure 7A:
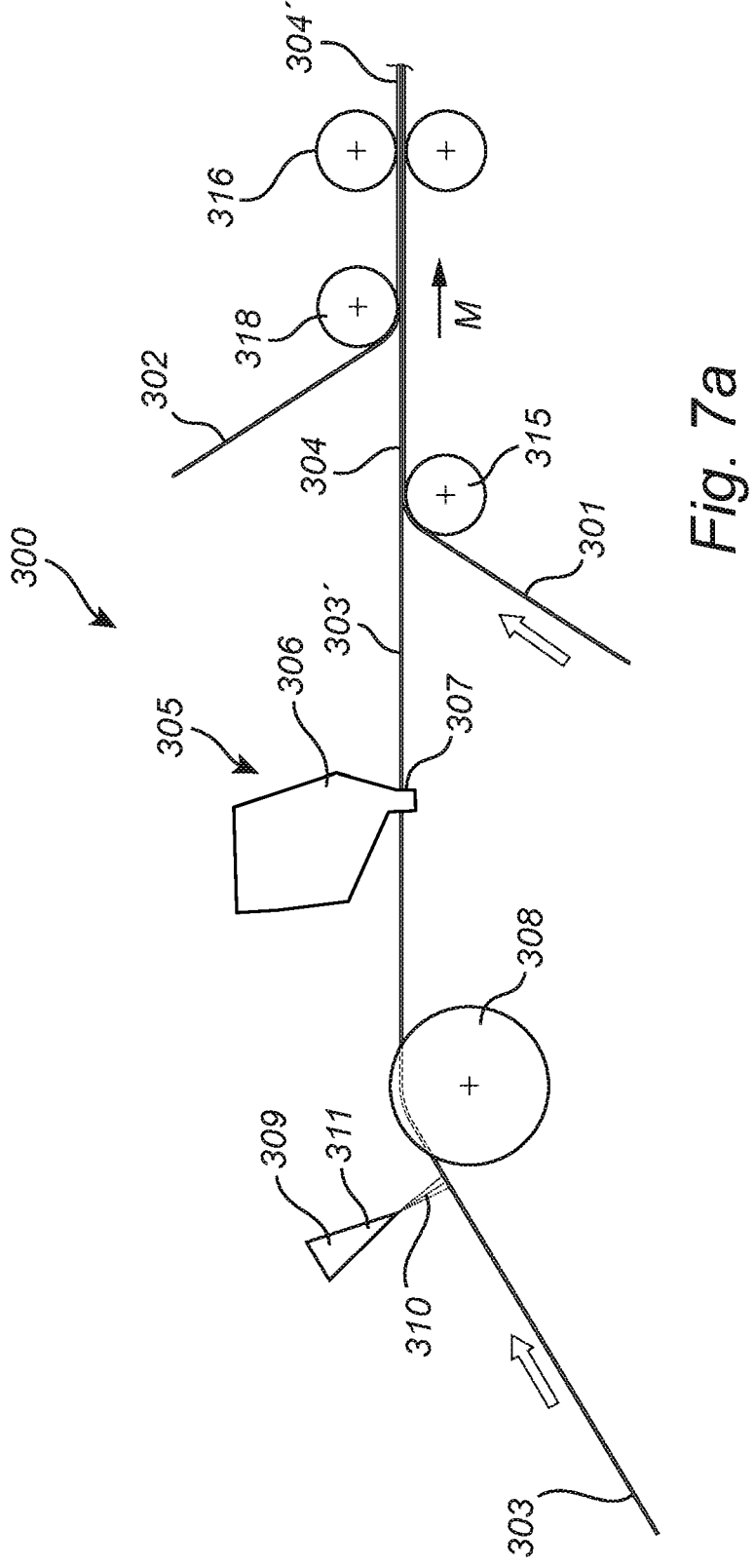
FIG. 7a schematically shows a first example embodiment of the apparatus which can be used in the manufacturing process shown in FIG. 3 from the side.
Figure 7B:
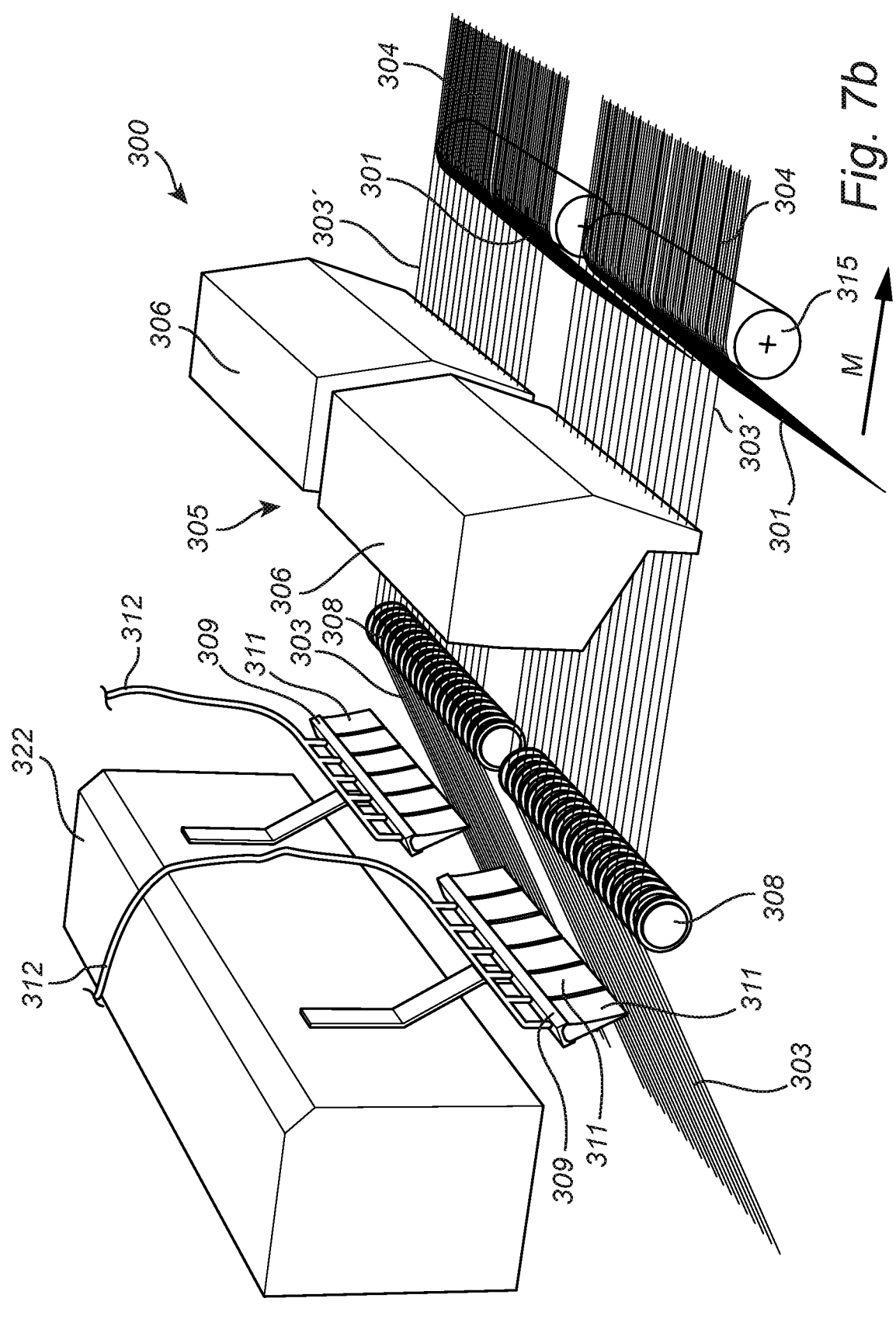
FIG. 7b schematically shows the first portion of the apparatus in FIG. 7a in perspective from a top view.

An example embodiment of a method and apparatus for manufacturing the laminated product having the strips 39, 40, 41, 43, 44 of elastic material sandwiched between the first web section 38a and the third web section 45a, and also between the second web section 38b and the fourth web section 45b using adhesive is schematically illustrated in FIGS. 7a and 7b.

In order to form the crotch portion 5 (see FIG. 1) with its absorption body 17, a third continuous sheet 46 of web material is provided and forms the basis of a backsheet for the crotch portion 5. The absorption body 17 is then laid out on the third continuous sheet 46. Also, a seventh strip 47 and an eighth strip 48 of elastic material are also laid out on the third sheet 46 of web material. The seventh strip 47 of elastic material forms the basis of the first absorbent body elastic 25 (see FIGS. 1 and 2), whereas the eighth strip 48 of elastic material forms the basis of the second absorbent body elastic 26.

Next, a fourth continuous sheet 49 of web material is provided and is joined to the third continuous sheet 46, suitably in a manner which is similar to that described above with reference to the first web section 38a, the second web section 38b, the third web section 45a and the fourth web section 45b. During this process, the seventh strip 47 and eighth strip 48 of elastic material, forming leg elastics, as well as the absorption body 17, are sandwiched between said third continuous sheet 46 of web material and said fourth continuous sheet 49 of web material.

A folding procedure is next carried out so as to fold the edges of the crotch portion 5 and form the crotch edge 28, 29 (see FIG. 1) on the crotch portion. This folding operation is indicated in a simplified manner with the arrows 50 and 51 in FIG. 3. Similarly, folding of the front portion 3 and the back portion 4 is indicated in FIG. 3 with arrows 53, 54 in a simplified manner.

Figure 8:
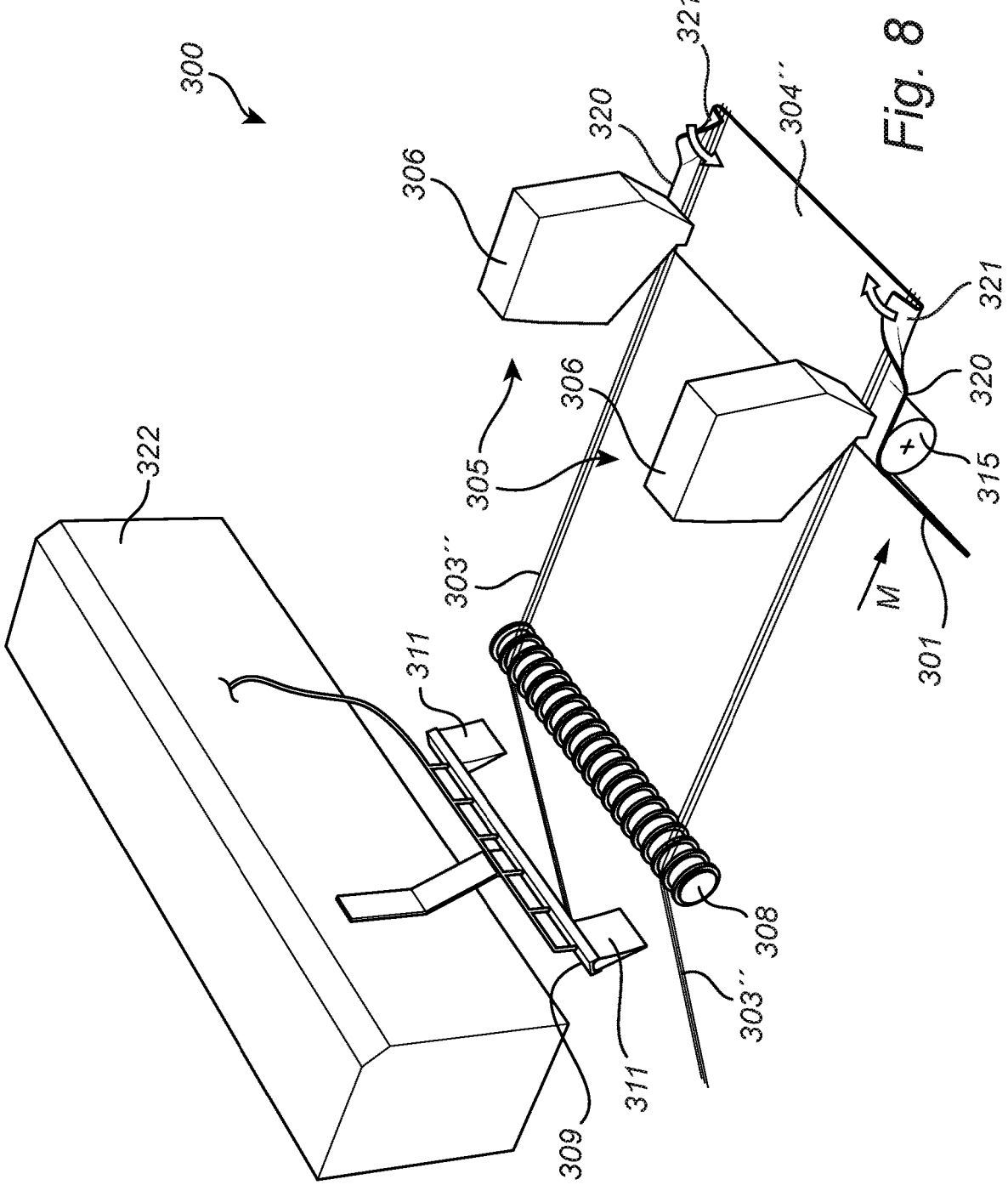
FIG. 8 shows a second example embodiment of an apparatus which can, for example, be used to manufacture leg elastic for an absorbent article.

An example embodiment of a method and apparatus for manufacture the leg elastics for the crotch portion 5 is schematically illustrated in FIG. 8. However, in FIG. 8 the fourth continuous sheet 49 has not yet been provided. It may be provided in a later stage or may be added before the folding operation. If it is added before the folding operation further adhesive may be needed to keep the folded portion in a folded position.

In a further manufacturing step (see FIG. 3) the web formed by means of the third sheet 46 of web material, the fourth sheet 49 of web material 49 and the absorption body 17, is cut into individual pieces 52, each of which forms the above-mentioned crotch portion 5 which is subsequently attached to the web formed by the first and second web sections 38a, 38b and the third and fourth web sections 45a, 45b. In this regard, the crotch portions 5 are laid out at a predetermined distance so as to bridge the front portion 3 and the back portion 4 and to form the basis of the finished absorbent article. As shown in FIG. 3, a piece 52 which forms a crotch portion 5 is laid out in a transversal direction in relation to the webs forming the front portion and the back portion.

The crotch portion 5 may be attached to the chassis using any known fastening technology, such as ultrasonic bonding, welding, adhesive, embossing, mechanical fastening, or the like. In this manner, a complete chassis is formed for the article 1.

In a subsequent manufacturing step, leg openings 55 are cut out of the laminated web material forming the chassis of finished absorbent products. The cutting may be performed by any type of suitable cutting equipment (not shown in FIG. 3), such as rolling cutting using two opposite rollers.

Next, the first and fourth web sections 38b, 45b are folded to form the final product, such that the first web section 38b becomes a backsheet of the chassis and the fourth web section 45b becomes the topsheet of the chassis.

This folding is shown with an arrow 56 in FIG. 3. After for example welding of side seams, the continuous assembly of products is cut into individual absorbent articles by means of cutting equipment (not shown in FIG. 3).

Figure 4:
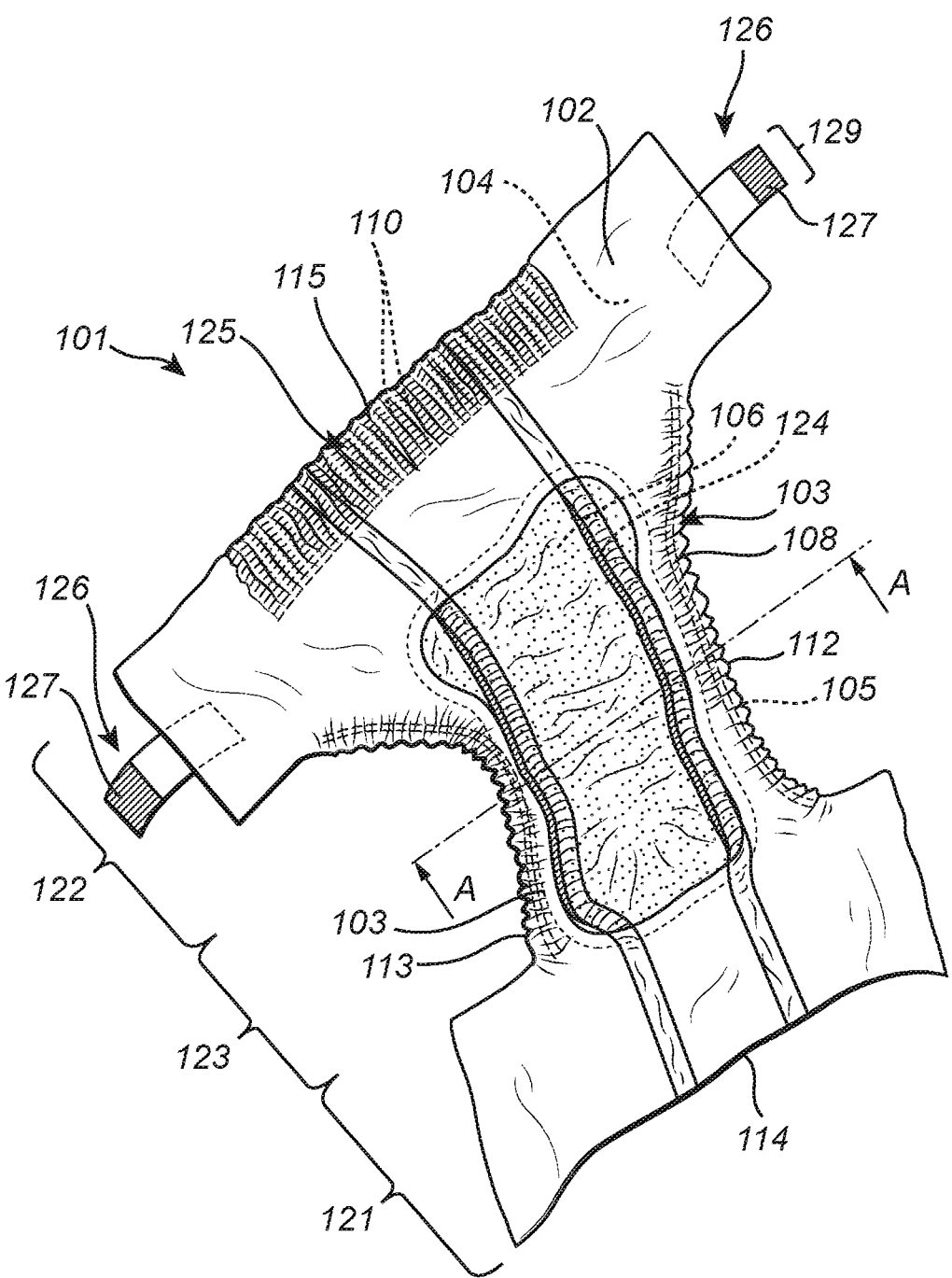
FIG. 4 schematically shows a perspective top view of an all-in-one absorbent article i.e. an open diaper.

FIG. 4 shows a so-called all-in-one absorbent article i.e. an all-in-one diaper. Also called open diapers. Diapers of that type are characterized in that they comprise fastening tabs, by means of which the front and rear waist section of the diaper is attached when the diaper is applied around a wearer's waist. FIG. 4 depicts various components of the all-in-one diaper 101.

The diaper 101 is an open diaper of the so-called all-in-one type. The diaper 101 is not joined together in the waist section at the time of sale, but is instead intended to be put on around a wearer's trunk and then to be joined together around the wearer's waist. This type of open diaper 101 is in widespread use for both infants and incontinent adult wearers.

The open diaper 101 essentially possesses the shape of an hourglass and exhibits longitudinal edges 112, 113, a front transverse edge 114 and a rear transverse edge 115. The open diaper 101 also exhibits a front edge section 121, a rear end section 122 and a narrower crotch section 123 situated between the end sections 121, 122. The crotch section 123 is intended to be situated in the narrowest area between the wearer's thighs during use.

When the diaper 101 is being worn, the front part of the crotch section 123 and the front end section 121 essentially function as a receiving area for urine, while the rear part of the crotch section 123 and the rear end section 122 essentially function as a receiving area for faeces.

The diaper 101 comprises a liquid-permeable covering layer 102, i.e. a topsheet, arranged over the surface of the diaper 101 which is intended to face towards the wearer during use, a backing layer 104, i.e. a backsheet, arranged over the surface of the diaper which is intended to face away from the wearer during use, an absorption body 106 enclosed between the topsheet 102 and the backsheet 104, and side flaps 103 arranged outside the absorption body 106.

The topsheet 102 of the open diaper 101 extends outside the absorption body 106 along the periphery of the entire absorption body 106. The topsheet 102 can consist of any material that is suitable for the purpose.

The backsheet 104 also extends outside the absorption body 106 and has the same extension as the topsheet 102.

The topsheet 102 and the backsheet 104 are connected to one another outside the absorption body 106, along the periphery of the entire absorption body 106. The topsheet 102 and the backsheet 104 can be connected to one another by a plurality of different means. Examples of such connecting means include gluing, thermal fusion, ultrasonic welding or the like.

Elastic components 105 are arranged outside the absorption body 106 in those parts of the side flaps 103 of the open diaper 101 which are oriented substantially in the longitudinal direction of the diaper 101. The elastic components 105 are leg elastics and have the task of preventing liquid and excrement from leaking out past the longitudinal edges 112, 113 of the open diaper 101 and in this way form outer liquid barriers 108 together with the surrounding layers.

The elastic components 105 consist of one or more elastic strands, which, in the extended state, have been applied between the topsheet 102 and the backsheet 104, at least in the crotch section 123 of the diaper 101. The elastic components 105 are attached to the backsheet 104 and the topsheet 102 by gluing. Alternatively, ultrasonic welding or the like can be used to attach the elastic components.

In alternative embodiments, the elastic components can be arranged on the side of the side flaps 103 that is intended to face towards the wearer during use, or on the opposite side of the side flaps, in which case they are naturally only attached to the topsheet 102 and the backsheet 104 respectively.

The elastic components in alternative embodiments can be constituted by elastic strip material, for example foam material, elastic nonwoven, elastic film, elastic laminate or the like.

In order further to prevent liquid or faeces from leaking out past the side edges 112, 113 of the diaper 101, the open diaper 101 is provided with inner side leakage barriers 124, i.e. standing gathers 124.

Figure 5:
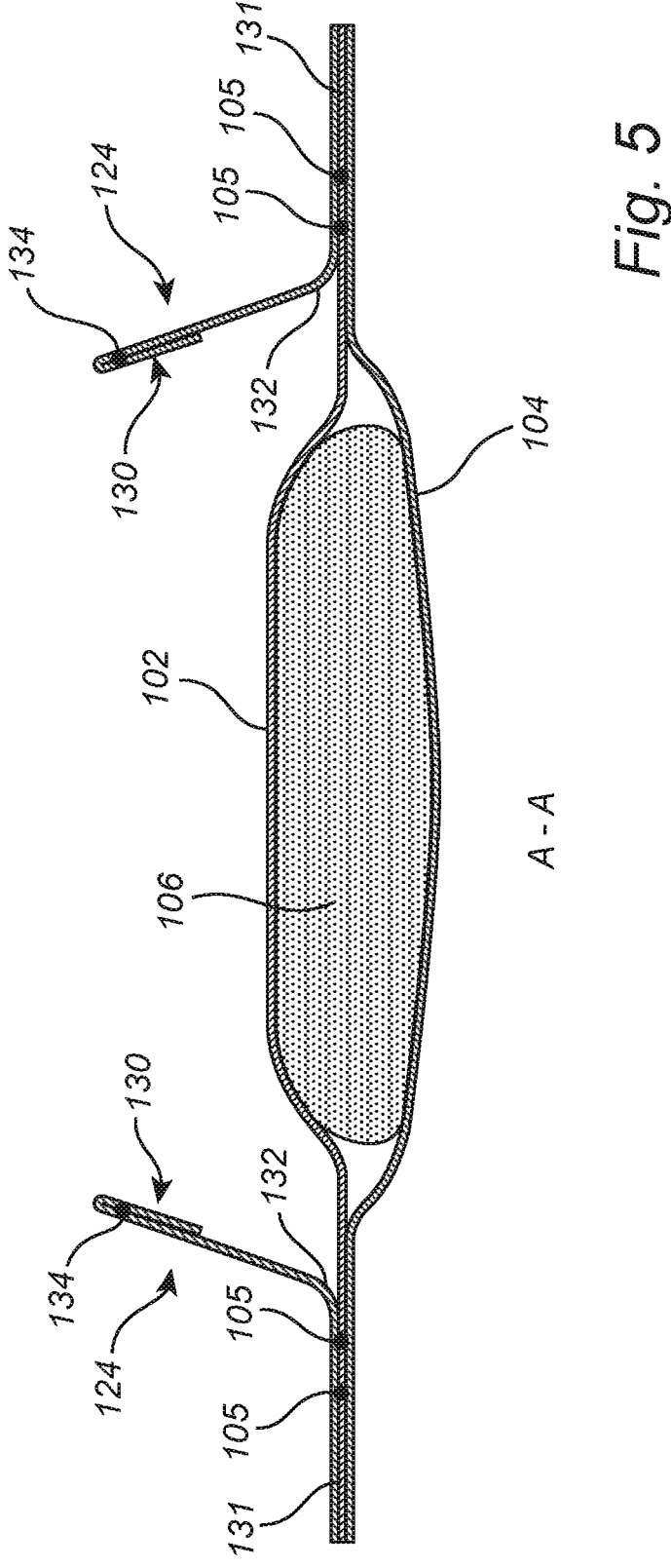
FIG. 5 shows cross-section A-A in FIG. 4

FIG. 5 shows the cross section A-A in FIG. 4 and shows the inner side leakage barriers, i.e. the standing gathers 124. Each standing-gather 124 has a free-standing first end edge region 130 and a second end edge region 131 attached at least to the backsheet 104 and/or topsheet 102. The free-standing first end edge region 130 extends freely from the proximal end 132 thereof. At the crotch region, the proximal end 132 is in this case located transversally inwardly of the leg elastic material 105.

The inner side leakage barriers, i.e. the standing gathers 124 comprise elastic elements 134 attached to the inner side leakage barriers 124 in a pre-tensioned state. The elastic elements 134 are preferably arranged close to the edge of the free-standing first end edge region 130. When the pre-tensioned elastic elements 134 are released, they are caused to contract together with the free-standing first end edge region 130, the inner side leakage barriers 124 being brought into a raised configuration away from the topsheet 102, at least in the crotch area 123 of the diaper 101 (see FIG. 4), where the side leakage barriers 124 are not folded down and attached to the topsheet 102.

The elastic elements 134 may be a strand, yarn or ribbon of elastic material extending in the longitudinal direction L of the diaper. The leg elastic material 105 may also be a strand, yarn or ribbon of elastic material extending in the longitudinal direction L. One or more strands, yarns or ribbons may be used to form elastic in each standing gather 134 and in each leg elastic 105.

The standing gathers may comprise of any of the materials described above for, for example, the topsheet or the backsheet. The standing gather may, for example, comprise of a sheet material of nonwoven material, such as a spun-bond material.

As seen in FIG. 4 the rear end section 122 of the diaper 101 is provided with waist elastic 125, which permits soft and flexible enfolding of the diaper around a wearer.

The waist elastic 125 in the example depicted here has a number of strand-shaped, essentially parallel-oriented elastic elements 110, which extend parallel to the rear transverse edge 115 of the open diaper 101.

The elastic elements 110 are arranged between the topsheet 102 and the backsheet 104 and are anchored in their extended state to the two layers 102, 104, whereby a retaining is obtained which tightens the diaper 101 around the waist of a wearer. When the elastic elements 110 contract, the two layers 102, 104 are wrinkled as illustrated in the figure.

In alternative embodiments, it is possible to conceive that the waist elastic may be formed of a prefabricated, separate waistband, in which case the elastic elements 110 have been anchored between two separate strips of material or a folded strip of material. The elasticated waistband has then been attached to the backsheet of the diaper and/or the topsheet. The waistband can be manufactured in the machine that is used to produce the diapers, or it can be manufactured in advance, in which latter case it is conveniently supplied in the form of a roll to the machine which manufactures diapers.

In other alternative embodiments, it is conceivable for the front end section 121 of the diaper also to comprise waist elastic 125, which further increases the softness and flexibility of the open diaper 101 when the diaper encircles a wearer. Such additional waist elastic can be achieved alternatively with types of elastic materials other than the strands depicted here and can comprise elastic film, elastic nonwoven, elastic foam or various kinds of elastic laminate in the same way as the leg elastic.

Arranged in conjunction with the rear end section 122 are two fastening tabs 126 for holding the diaper 101 securely around a wearer. One fastening tab 126 in this case is arranged on each side section of the rear end section 122. The fastening tabs 126 connect the rear end section 122 to the front end section 121 when the open diaper is being worn by the fastening tabs 126 exhibiting securing devices 127, which are capable of being affixed to a receiving part arranged on the front end section 121 of the diaper 101. The fastening tabs can be elastic.

The securing devices 127 may include male parts made of a hook-and-loop material and are attached to the fastening tabs 126, for example by means of an adhesive on the side of the fastening tabs 126 which face towards the receiving part when the diaper 101 is being worn. The receiving part, which is not illustrated in FIG. 4, for the fastening tab 126 has a strip of a receiving material that is adapted to the securing device 127 of the fastening tab 126.

The receiving part extends substantially parallel to the front transverse edge 114 on the side of the diaper that faces away from the wearer during use, that is to say on the side of the backsheet 104 that is oriented away from the absorption body 106. In the illustrative example described here, the material in the receiving part consists of a female part made of a hook-and-loop material and is appropriately designed so that its extension in the longitudinal direction of the diaper 101 coincides with the width 129 of the fastening tabs 126. The receiving part extends essentially over the width of the entire diaper 101 in the transverse direction of the diaper 101.

In alternative illustrative embodiments of a diaper, it is possible to conceive the arrangement of separate receiving parts for the respective securing device 127, the receiving parts being arranged in conjunction with the longitudinal edges 112, 113 of the diaper on the front transverse edge 114 of the diaper 101. In other alternative embodiments, the backsheet 104 can be adapted to interact with the securing devices 127 of the fastening tabs 126, in which case no special receiving part is required.

When putting the open diaper 101 on a wearer, the open diaper 101 is positioned between the wearer's legs in the area of the wearer's crotch. The diaper 101 is then closed around the wearer's waist by causing the fastening tabs 126 to overlap the front end section 121, so that the securing devices 127 of the fastening tabs 126 can be applied to the receiving part in order to hold the diaper securely.

The fastening tabs 126 are attached to the rear end section 122 in connecting areas which are located in those areas of the rear end section 122 which lie next to the side edges 112, 113 running in the longitudinal direction.

Material combinations are usually selected so that the connection between the securing devices 127 and the receiving part can be opened and reclosed to permit inspection of the open diaper 101 when it is being worn.

Figure 6:
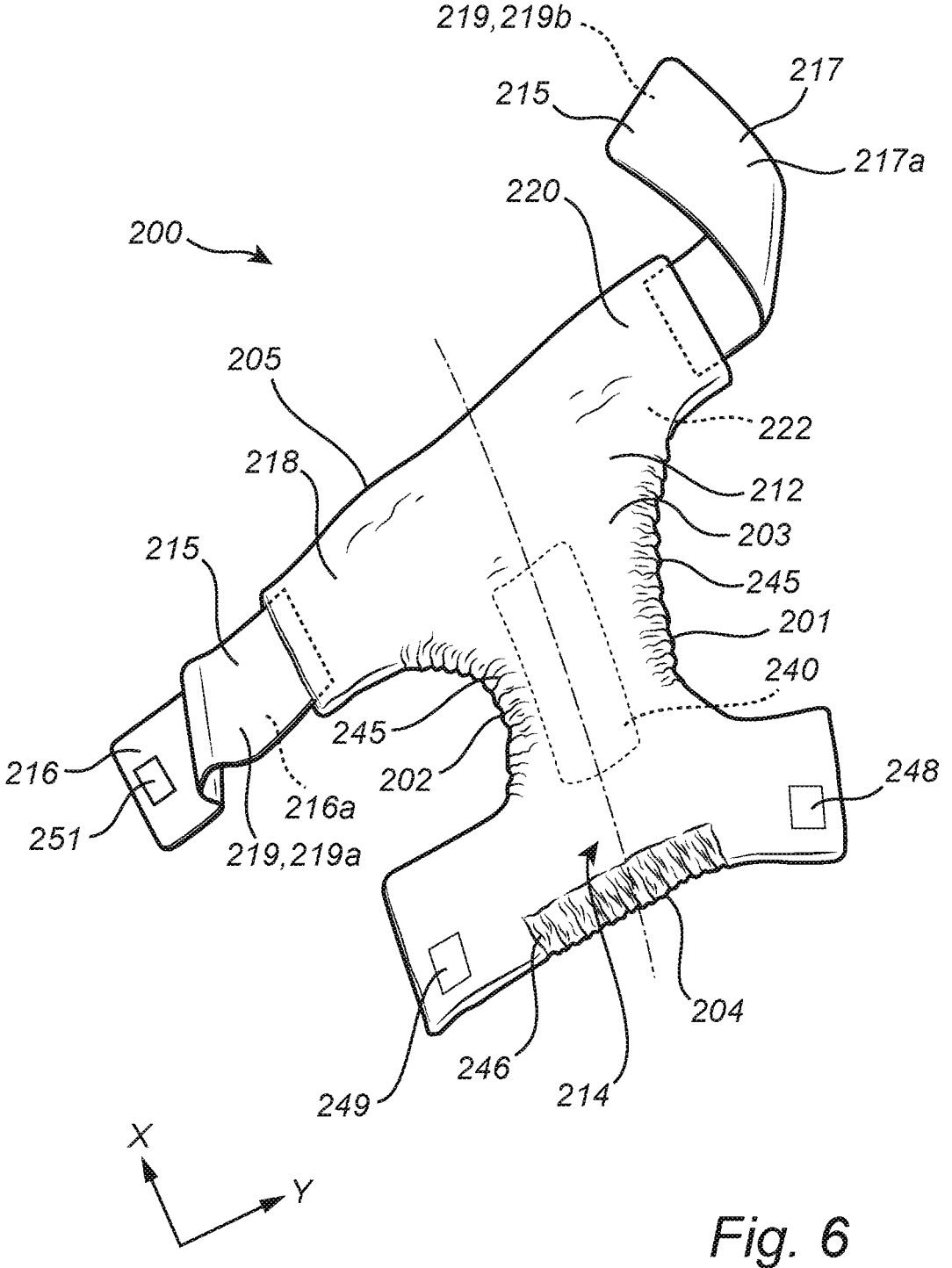
FIG. 6 shows a perspective top view of a belt type absorbent article, i.e. a belted diaper.

FIG. 6 shows a so-called belt type absorbent article 200, i.e. belted diaper which is shown from the side which is intended to face towards the wearer when in use.

The belt type absorbent article 200 comprises a chassis 212 and a waist belt 215. The belt 215 in this example embodiment includes a first belt portion 216 and a second belt portion 217. Further, the belt type absorbent article 200 has a longitudinal direction X and a transverse direction Y.

Moreover, the chassis 212 has a first end portion 218, a second end portion 214 and a central portion 203 extending therebetween. The first end portion 218 may be the rear region, also called back region. The second end portion 214 may be the front region. Alternatively, it may be the other way around. The central portion is the crotch region connecting the front and the back region. In this example embodiment, the first end portion is the back region 218 and the second end portion is the front region 214.

Typically, the article comprises a body-oriented surface 220 facing the wearer during use and a garment-oriented surface 222 facing away from the wearer in use.

The chassis includes a topsheet 220, which forms the body-oriented surface 220 intended to face towards the wearer. The chassis also includes a backsheet, which forms the garment-oriented surface 222 intended to face away from the wearer in use. An absorption body 240 is arranged between the topsheet 220 and the second substantially liquid-impermeable backsheet 222.

The first and the second belt portions 216, 217 are attached to the chassis 212 so that the first belt portion 216 and the second belt portion 217 extend on each side of the first end portion 218 of the chassis for securing to each other around a waist of a wearer of the article to form the belt having an exterior surface 216a, 217a. Thus, each first and second belt portions 216, 217 are connected to the chassis 212 in the rear region 218, respectively.

Typically, although not strictly required, the belt portions may be partly or entirely elastic. Thus, hereinafter, the waist belt may sometimes also be referred to as the belt. The belt 215 of the belt type absorbent article 200 is intended to encircle a wearer's waist. In other words, the belt portions 216, 217 forming the belt are intended to encircle a wearer's waist. The belt here has an inner surface 219 facing the wearer during use and an outer (exterior) surface 216a and 217a facing away from the wearer during use, wherein said belt comprises the first belt portion 216 and the second belt portion 217. Thus, the first belt portion has an inner surface 219a facing the wearer during use. Likewise, the second belt portion has an inner surface 219b facing the wearer during use. In the belt article shown in FIG. 6 the belt portions (first belt portion 216 and second belt portion 217) extend in the transverse direction Y of the belt article. The belt portions (first belt portion 216 and second belt portion 217) extend also in the longitudinal direction X.

The first belt portion 216 and the second belt portion 217 are attached to the chassis 212 so that said first belt portion 216 and said second belt portion 217 each extends on each side of the first end portion of the chassis for securing to each other around a wearer of the article. To this end, as will be further described hereinafter, the first belt portion 216 has a fastener 251 or a fastening component adapted to be attached to second belt portion 217 for securing the belt portions to each other around the wearer of the article.

In this example, the fastener is configured to be releasably attached to the surface 217a. Accordingly, the fastener is a so called "refastenable" fastener configured to be refasten to another part of the article to form an interconnection between the mating components. Hence, the fastener is typically adapted to be attached in a refastenable manner, as is well-known. The exterior surface 217a of the other of the belt portions may in some examples be provided with a mating fastening component (not shown).

Further, each one of fastener 251 and the mating fastening component may comprise a mechanical connector structure being capable of forming a mechanical interconnection with each other. One example of a mechanical connector structure is a hook and loop material. Hereby, the fastener and the mating fastening component are mechanically connectable to form an interconnection between said first belt portion and said second belt portion for securing to each other around a wearer of the absorbent article. The interconnection may sometimes be referred to as refastenable connection.

As mentioned above, the second end portion 214 of the chassis comprises a fastening device 248, 249 for securing the second end portion 214 of the chassis to the belt portion so that the article assumes a pant-like shape with the belt portions forming a part of a waist portion of the pant. The second end portion 214 of the chassis is typically secured to the exterior surfaces 216a, 217a of the first belt portion 216 and/or second belt portion 217. In other words, the front region, i.e. second end portion 214 of the chassis in FIG. 5 includes the fastening device(s) 248, 249 for securing the front end part of the chassis to the belt.

To improve the fit of the belt type absorbent article 200, the longitudinal edges 201, 202 of the topsheet 220 can be provided with leg elastic 245 arranged substantially in the longitudinal direction X of the article. The task of the leg elastics 245 includes improving the fit of the article and making the belt article 200 more like textile multiple-use briefs/pants. The respective leg elastic 245 can comprise one or more elastic strands that in the extended state have been joined to the topsheet 220 by gluing, ultrasonic welding or the like. Alternatively, the respective leg elastic 245 can take the form of elastic ribbon material of foamed material, for example. The respective leg elastic 245 may be arranged on the side of the topsheet 20 that is intended to face away from the wearer when in use.

The belt type absorbent article 200 may also have standing gathers (not shown).

The rear or front regions 218, 214 of the belt type absorbent article 200 can also be provided with so-called waist elastic 246 in the form of elastic elements arranged along a second transverse edge 205 or a first transverse edge 204 of the belt type absorbent article 200 to give the belt article 200 a soft, flexible enclosure of the wearer's waist. In FIG. 6 only the front end part 214 of the belt article 200 is provided with waist elastic 246. The waist elastic 246 is in the form of a thin strip of elastic foam material that is attached by glue to the side of the topsheet 220 that is intended to face away from the wearer. The waist elastic 246 can also comprise of one or more elastic strands that in the extended state have been joined to the topsheet 220 by gluing, ultrasonic welding or the like. The waist elastic 246 is applied in a stretched state to achieve a holding-together force that stretches the belt type absorbent article 10 around the wearer's waist.

When a belt type absorbent article 210 is to be applied to a wearer, the belt portions 216 and 217 (forming the belt 215) is first fixed around the wearer's waist. The front region 214 of the belt article 210 that hangs loosely is then led in between the wearer's legs, following which the fastening device 248, 249 is fixed to the belt portions 216 and 217 (i.e. the belt 215) on the stomach on the side of the belt 215 oriented away from the wearer. The hook elements of the fastening device are fixed in this case to loops arranged on the surface of the belt 215 oriented away from the wearer, e.g. belt portion surfaces 216a and 217a. A belt type absorbent article is also conceivable in which the belt is connected to the front end part of the belt article. Such an article is applied to the wearer in the reverse manner, i.e. after the belt has been fixed around the wearer's waist, the loosely hanging rear end part is led in between the wearer's legs and fixed to the belt at the back on the side of the belt oriented away from the wearer.

The topsheet in all absorbent articles described above and shown in FIGS. 1-6 is a liquid permeable topsheet arranged at the boldfacing side of the disposable absorbent hygiene product. Materials suitable for topsheets are commonly known in the art of disposable absorbent hygiene products, and for the purposes of the present disclosure any material commonly known for use as a topsheet materials may be used, including, but not limited to non-woven materials and perforated polymeric films.

The topsheet is suitably sufficiently fluid permeable to allow discharged body fluids such as urine to penetrate through the thickness of the topsheet. Also, the topsheet is suitably manufactured from a material which is compliant and soft feeling to the skin of the wearer.

The topsheet may be manufactured from various web materials such as woven and nonwoven webs, perforated films, open cell foams, or combinations or laminates of the above-mentioned materials.

In the context of the present disclosure, a "nonwoven" is a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes such as meltblowing, spunbonding, solvent spinning, electrospinning, and carding.

A nonwoven material suitable as a topsheet can be manufactured from synthetic fibres such as polyester or polypropylene, or natural fibres such as cotton fibres. A mix of synthetic and natural fibres may also be used.

The nonwoven materials to be used for the topsheet may for example be made of a spunbond, a spunbond/spunbond composite or a spunbond/meltblown composite, such as a SMS (spunbond/meltblown/spunbond), SSMS, SSMMS, SMMS, nonwoven material of polypropylene or bicomponent fibers of polypropylene and polyethylene, or of a combination of such materials. The topsheet may also have elastic properties.

The topsheet may be hydrophilized in order to improve the tendency for urine to penetrate the topsheet into the underlying structures. Methods for hydrophilizing nonwovens are known and include coating the nonwoven material with a hydrophilic coating, such as by applying a surfactant coating; by applying a hydrophilic monomer composition and a radical polymerization initiator onto the nonwoven followed by initiating a polymerization reaction on the nonwoven; by applying a coating of hydrophilic nanoparticles; or by treating the nonwoven surface with a high energy treatment (corona, plasma).

A surfactant coating may be obtained for example by applying a surfactant composition to the non-woven material by any suitable means including spraying, slot coating, kiss roll coating and/or soaking the material in a bath containing the surfactant. The hydrophilization treatment may be performed in-line during assembly of the absorbent article, or may performed separately and the topsheet may then delivered as ready-to-use rolls to the disposable absorbent hygiene product manufacturing plant.

The topsheet material may have a basis weight of from 8 to 20 g/m2, such as from 12 to 17 g/m2. However, the disclosure is not limited to topsheet materials having this basis weight only.

The backsheet, in all absorbent articles described above and shown in FIGS. 1-6 is arranged at the garment facing side of the disposable absorbent hygiene product. Materials suitable as backsheets are commonly known in the art of disposable absorbent hygiene products. The backsheet prevents the exudates absorbed by the absorbent assembly from soiling other external articles that may contact the disposable absorbent hygiene product, such as bedsheets and undergarments. The backsheet may be substantially impermeable to liquids, such as urine.

The backsheet may be substantially liquid impermeable but breathable, i.e. gas permeable, implying that air and other gases may pass through the backsheet while being substantially impermeable to liquids.

Any material commonly known for use as a backsheet materials may be included in the backsheet, including but not limited to polymeric films, for example films of polyethylene, polypropylene or copolymers of polyethylene or polypropylene, hydrophobized nonwoven materials, fluid impermeable foams and fluid impermeable laminates.

The backsheet may comprise one or more layers of material. For example, the backsheet may be a laminate of a liquid impermeably polymeric film towards the absorbent assembly and nonwoven towards the garment side, to provide a textile, soft feeling to the outer surface of the disposable absorbent hygiene product.

It is also contemplated that the backsheet may be made or otherwise include an entirely or partially elastic material in order to give the product a better fit when in use.

The absorption body, also called absorption core, in all absorbent articles described above and shown in FIGS. 1-6 can comprise one or more cores. The cores can be constructed from one or more layers of cellulose fluff pulp. The cellulose fluff pulp can be mixed with fibers or particles of a highly absorbent polymer material, so-called superabsorbent polymers, of the type that chemically binds large quantities of fluid on absorption with the formation of a fluid-holding gel. The core can also comprise highly absorbent polymer material arranged in a layer inside the core or connected to the surface or surfaces of the core. The core can further include further components for improving the properties of the core. Examples of such components are binding fibers, various types of fluid-dispersing layers or fibers, dimensionally stabilising components, reinforcing fibers or the like.

Superabsorbent polymers are well-known in the field of absorbent products and are used to help improve the absorbent properties of such products. Superabsorbent polymers are constituted by water-swellable and water-insoluble polymers that are capable of absorbing large quantities of fluid upon formation of a hydrogel, such as capable of absorbing at least 5 times their weight of an aqueous 0.9% saline solution as measured according to the method NSWP 241.0.R2 (15). The superabsorbent polymer polymers may be inorganic or organic crosslinked hydrophilic polymers, such as polyvinyl alcohols, polyethylene oxides, crosslinked starches, guar gum, xanthan gum, crosslinked polyacrylates, and the like. The polymers may be in the form of powders, granules, microparticles, films, foams and fibers, for example. Upon contact with fluids, such super absorbent polymers swell by absorbing the fluids into their structures. In general, super absorbent polymers can quickly absorb fluids insulted into such articles, and can retain such fluids to prevent leakage and help provide a dry feel even after fluid insult.

The type of super absorbent polymer may be the same or may vary within the core. For example, a super absorbent polymer with a first set of characteristics may be used in the front and back regions of the absorption body, or in a first core, and a super absorbent polymer with a second set of characteristics may be used in the central region of the absorption body, or in a second core.

An acquisition layer can be arranged between the topsheet and the absorption body. Materials suitable as acquisition layers, also referred to in the art as transfer layer, or ADL (acquisition and distribution layer), are commonly known in the art of disposable absorbent hygiene products, and for the purposes of the present disclosure, any material known to the person skilled in the art as being useful as an acquisition layer may be used. An acquisition layer may for example be in the form of an airlaid layer, a spunlace layer, a high-loft, foam or any other type of material layer which may be used in an absorbent article to act as a liquid acquisition and absorption layer. The acquisition layer is suitably adapted to quickly receive and temporarily store discharged liquid before it is absorbed by the absorbent core. Such acquisition layer may be composed of for example airlaid nonwoven, spunlace nonwoven, high loft nonwoven or foam materials. An airlaid nonwoven may be produced with fluff, wood pulp, and here the fluff fibers are dispersed into a fast-moving air stream and condensed onto a moving screen by means of pressure and vacuum. The acquisition layer may preferably be of an air-through bonded nonwoven of polyester fibers.

The term "nonwoven", mentioned in relation to different parts of the disposable absorbent article disclosed in FIGS. 1-6 such as topsheet and/or backsheet, which in term of their properties are located between the groups of paper and cardboard on the one hand and textiles on the other hand. As regards nonwovens, a large number of extremely varied production processes are used, such as airlaid, wetlaid, spunlaced, spunbond, meltblown techniques etc. The fibers may be in the form of endless fibers or fibers prefabricated with an endless length, as synthetic fibers produced in situ or in the form of staple fibers. Alternatively, they may be made from natural fibers or from blends of synthetic fibers and natural fibers.

Further components commonly employed in disposable absorbent hygiene products shown but not illustrated in the figures of the present disclosure may be employed in a disposable absorbent hygiene product according to the present disclosure.

A wetness indicator, for example a material that changes its color upon contact with urine, may be included in the disposable absorbent hygiene product, such as disposed between the absorbent assembly and the backsheet and visible through the backsheet, such as to indicate whether a wetting event has taken place.

FIG. 7a and FIG. 7b shows schematically an apparatus 300 for producing two elastic laminates 304' parallel to each other. For example, it could be used to manufacture the elastic laminates of the absorbent pant shown in FIGS. 1 and 2 and which manufacturing process is shown in FIG. 3. FIG. 7a show the apparatus in FIG. 7b from the side, but with some additional parts which are not shown in FIG. 7b. Each laminate 304' comprises a plurality of elastic strands 303 between two continuous sheets 301 and 302 (see FIG. 7a, since FIG. 7b shows only the first part of the apparatus).

Figure 9:
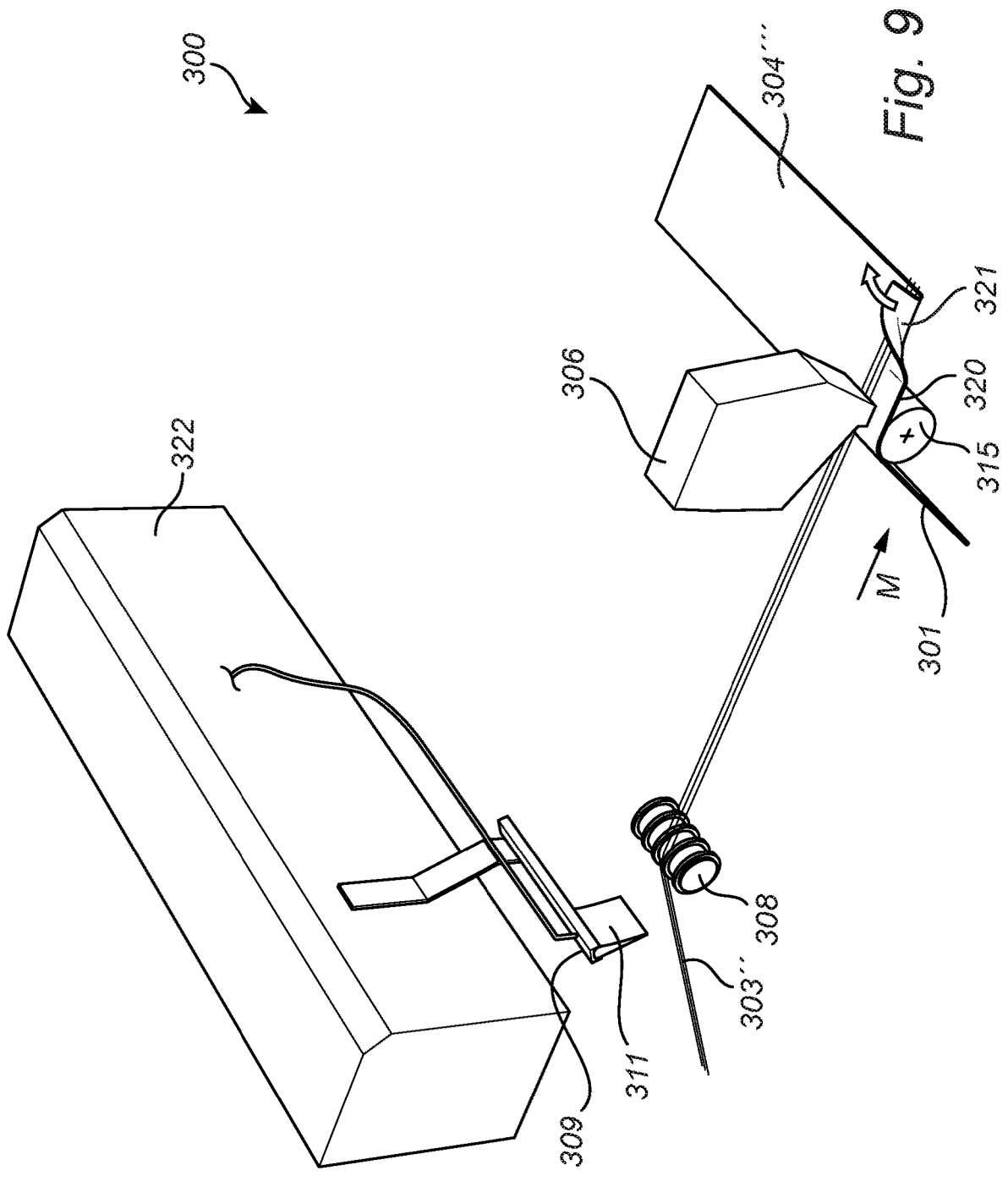
FIG. 9 shows a third example embodiment of an apparatus which can be used to manufacture, for example, a standing gathers to be used in an absorbent article.

As can be seen in FIG. 7b, which shows the first part of the apparatus in 7a, the two elastic laminates 304, 304' are produced parallel and independent of each other. Hence the apparatus 300 in FIG. 7b comprises double of each device making up the apparatus 300. That is the apparatus 300 comprises two blowing devices 309, two guiding rolls 308, two adhesive nozzles 306, two supporting rolls 315 etc. The apparatus will only be described in regard to making one elastic laminate. For the other elastic laminate the same applies. The apparatus 300 is not limited to having double of each device making up the apparatus. If only one elastic laminate is going to be produced only one of each device may be necessary. This might be the case when producing a standing gather, which is shown in FIG. 9.

For producing an elastic laminate 304' a first continuous sheet 301 is fed from a nonwoven web roll by a first feeding device (not shown) in the machine direction M, they may pass through dancer cylinders (not shown) known in the art and will hence not be further described in order to be sufficient tensioned.

A plurality of elastic strands 303 are fed in parallel from a multi-strand roller by a second feeding device (not shown) in the machine direction M. The strands 303 are spaced from each other, and they may be from about 1-20 strands per centimetre, for example from 1 to 10 strands per centimetre and specifically from 2 to 6 strands per centimetre. The spacing between the strands in the laminate may be for example of from about 0.5 to about 10 mm, whereby an elastic laminate with sufficient elasticity and comfort can be provided. The elastic strands 303 are tensioned by means of dancer rollers (not shown). The elastic strand, also called elastic thread is made of elastic material, such as e.g. natural or synthetic rubber, thermoplastic elastomers, such as ther-moplastic polyurethane or styrene block co-polymers or elastane, also referred as to spandex (polyurethane-polyurea copolymer). The strands may be of the elastane type that is available under the trade name "LYCRA", but any suitable elastic strand may be used. The strands may have a linear mass density, dtex, of about 80-800 dtex.

The elastic strands are elongated during the production process. They may be elongated from about 30 to about 300% of the initial, non-tensioned original length, for example from about 70-250% and specifically from about 100 to about 200% of the initial, non-tensioned original length. The elastic strands may be of a type that able to tolerate an elongation of at least about 200% without break-ing, so that they can be safely used in the production process without risk of breaking. Improved fit of an absorbent product can be created by controlling the distance between, linear density, and the pre-strain of the elastomeric material in relation to each other and to the openings for the body. This may occur by choosing different materials throughout the elastic laminate that exhibit desired properties. The different materials are combined at specific distances, linear densities, and prestrains to create an elastic laminate that may act to dynamically create fitment forces in a product.

The elongated, i.e. stretched, elastic strands are guided via an elastic strand guide 308, which here is exemplified as a guiding roll 308, towards an adhesive dispensing system 305. The guiding roll 308 is a rotatable roll having grooves on its outer circumferential area. Each elastic strand is arranged in a respective groove. As an alternative to one larger guide roll several rotatable guide rolls can be con-nected together and which rotates independently of each other. Each guide roll may have one or more grooves for the elastic strands to be arranged in.

The adhesive dispensing system 305 comprises two nozzles 306 (see FIG. 7*b*) each comprising several liquid discharge passages 307 to dispense liquid adhesive onto the respective elastic strands 303. The number of liquid dis-charge passages may be the same as the elastic strands to be coated with the adhesive.

Each nozzle 306 is a slot coating nozzle including one or more grooves (not shown). Each groove configured to be filled with extruded adhesive from one liquid discharge passage 307 (see FIG. 7*c*). Each individual strand is coated separately, by the slot coating device which can be for example a V-slot or comb-slot-coating device. By the comb-slot or comb-coater is meant in this case a slot coater that is prepared with a shim that is designed in such way that it can be used as guiding device for the elastic strands. However, the device can also be a slot coater that is V-notched for each strand and with and without guiding device attached.

Such devices are delivered for example by the company Nordson Corporation of Amherst, Ohio (United States), and may be in the form, for example, of a device commercially available under the name Speed-Coat™ Slot applicator or a device commercially available under the name Universal™ Surewrap® Nozzles or a device under the name Allegro® Elastic Attachment Nozzles.

A stretched elastic strand moving through a groove will be surrounded with the extruded adhesive in the corresponding groove. Consequently, the stretched elastic strand is coated as the strand moves through the groove in the slit coating nozzle. It is however understood that other types of adhesive nozzles known in art can be used in order to provide the elastic strands with adhesive.

After the elastic strands 303 have received adhesive the elastic strands 303' are guided downstream to the first continuous sheet 301 to form an elastic laminate 304 com-prising the first continuous sheet and the elastic strands. The first continuous sheet 301 is guided to pass under the elastic strands 303 and to come in contact with the adhesive coated elastic strands 303' forming the elastic laminate 304. Hence, a first surface of the first continuous sheet 301 is joined to the elastic strands 301'. The elastic laminate 304 continues traveling in the machine direction M.

A second continuous sheet 302 is fed by a third feeding device (not shown) from a nonwoven web roll (not shown) and guided by a roll 318 to pass over the elastic strands 303' and to come in contact with the adhesive coated elastic strands 303'. Hence, a first surface of the second continuous sheet 302 is joined to the elastic strands 301'. Both continu-ous sheets define a width in the cross-machine direction. The cross-machine direction being the direction perpendicular to the machine direction M. Since only the elastic strands are coated with adhesive, the two continuous sheets 301, 302 are substantially free of adhesive outside the areas where the layers are attached to the elastic strands. The two continuous sheets 301, 302 may therefore not be in direct contact with each other at the adhesive bonding points, but may instead only be joined via the elastic strand.

After the first and second continuous sheets 301, 302 and the stretched adhesive coated elastic strands 303' are brought together they are compressed by a joining device 316 to form a laminate (see FIG. 7*a*). The joining device 316 comprises two rolls which form a pressure nip which secure the components together when they pass between the two rolls. After compression the elastic strands are relaxed in the formed laminate to form a corrugated elastic laminate with a predetermined corrugation pattern.

As an alternative to a second continuous sheet 302 the laminate 304' can be formed by folding the first continuous sheet to form a first layer fold, and directly joining the first continuous sheet and the first layer fold, wherein the first layer fold overlaps said at least one elastic strand. This is shown in FIG. 8 and FIG. 9.

The apparatus 300 in FIGS. 7*a* and 7*b* further comprises an air blowing device 309 which is a device that blows air 310 via air discharge passages 313 onto the elastic strands in order to blow off dust, loose fibers and other contaminants. The air blowing device 309 is arranged upstream of the nozzle 306 and above the elastic strands 303. It is mounted to a frame 322 (see FIG. 7b), only part of the frame 322 is showing. The air blowing device 309 is a separate device which means existing equipment/manufacturing lines may be easily supplemented with the air blowing device. The air blowing device 309 can hence be used on any machines or production line and is not dependent on a specific supplier of the machines or the supplier of the nozzle equipment. Further, having a separate air blowing device makes it easy to adjust placement of the air blowing device 309 it in the machine and provides easy adjustment to permit air to from the air blowing device at a specific angle relative to the elastic strand.

The elastic strand guide 308 is arranged between said nozzle 306 and said air blowing device 309. The elastic strand guide 308 is arranged closer to said air blowing device 309 than to said nozzle 306 and the air blowing device 309 blows air onto said elastic strand guide 308 and onto said elastic strand 303. This way any dust and loose fibres and/or other contaminants which may be on the elastic strand guide is simultaneously cleaned with the elastic strand and the elastic strand guide 308. The air blowing device 309 is arranged above the elastic strands and blows the air onto the top of the elastic strands 303. Alternatively, the air blowing device 309 may arranged underneath the elastic strands and blow the air from underneath the elastic strands 303 (not shown). This mean the cleaning of the elastics with air, can happen from below and from the top of the elastics. The air blowing device 309 may alternatively be arranged between the elastic strand guide 30, (exemplified here as a guiding roll 308) and the nozzle 306.

The position of the air blowing device 309 may be decided by the available space in the apparatus. For example, if an existing manufacturing line shall be supplemented with an air blowing device 309 there might only be space for an air blowing device 309 which is arranged above the elastic strands 303 or under the elastic strands 303.

Figure 10:
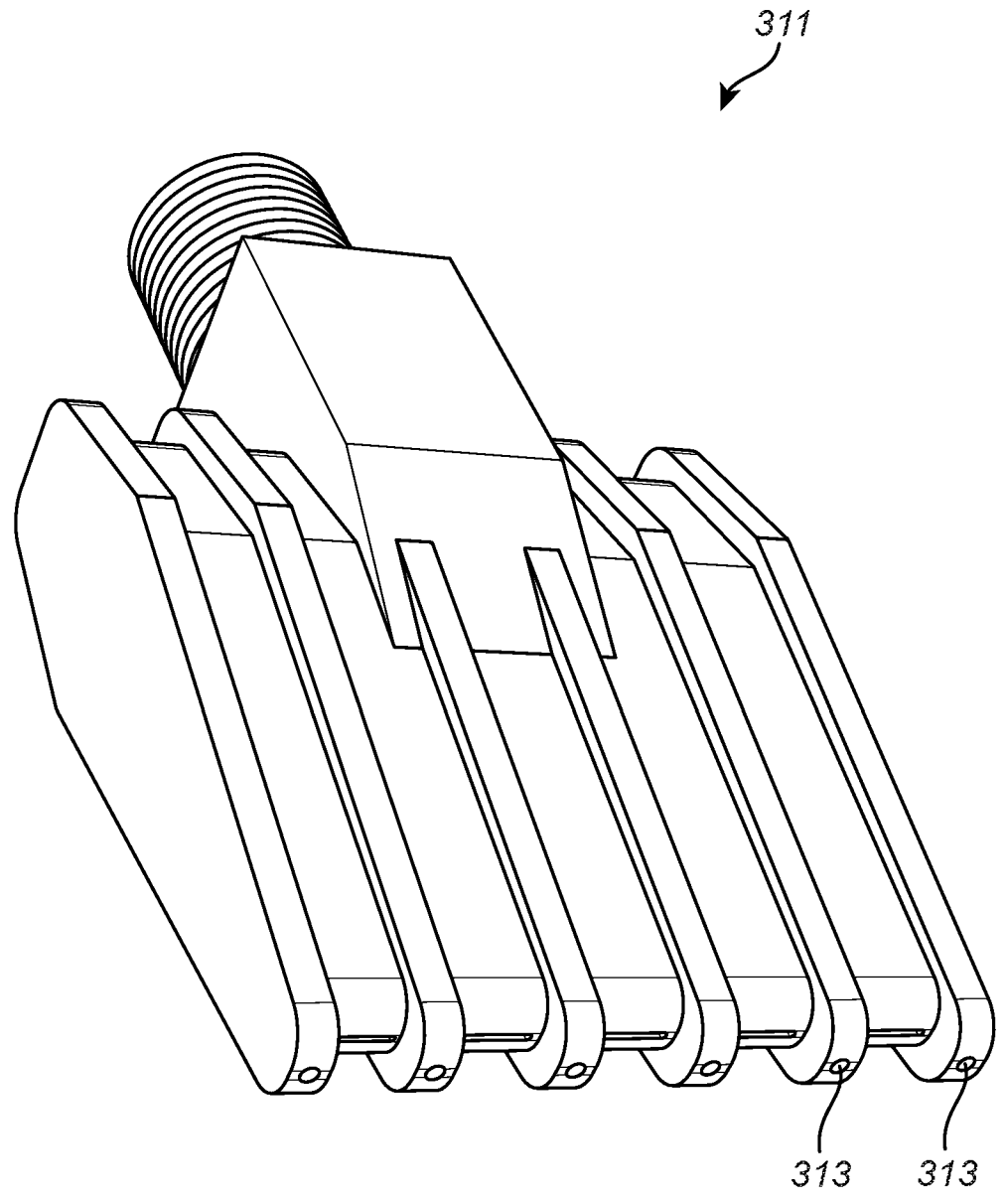
FIG. 10 shows an example of an air blowing device shown in FIGS. 7a-e, 8 and 9.

The air blowing device 309 may comprise one or several air blowing heads 311. The air blowing heads 311 are connected to a pressurized air source (not shown). In FIG. 7b six air blowing heads 311 are connected together and are fluidly connected to the pressurized air source via an air tube 312. An air blowing head 311 is shown in FIG. 10. Each air blowing head 311, as shown in FIG. 10, may comprise one or more air discharge passages 313 through which the pressurized air will pass. In FIGS. 7a and 7b and especially shown in FIG. 7c the air discharge passages 313 are directed towards the elastic strands so the air hits the elastic strand. Preferably, the number of air discharge passages 311 may be same as the number of elastic strands 303 which are going to be cleaned and the distances between the air discharge passages 313 may be the same as the distances between the elastic strands to be cleaned. Hence, air from one air discharge passage may clean one elastic strand. The air blowing device blows air through each air discharge passage 313 with an air pressure in the range of 0.5 to about 1.5 bar, specifically in the range of 1 to about 1.5 bar. This gives the air discharged from the air discharge passage a velocity having a magnitude sufficient to overcome the forces adhering the particulates to the elastic strand and removing particulates from the elastic strand. The air is cold. With "cold air" it is meant air that has not been intentionally heated, by a heating device or a component designed for that purpose. The air blowing device, in that regard, blows air that has not been purposely heated. That is, the air has not been heated by additional heating device. However, the air is not limited to be non-heated, the use of heated air is contemplated as well as an alternative.

The air blowing device may for example be an air knife from Silvent AB or several air nozzles, i.e. air blowing heads 311 as shown in FIG. 7b, which may be connected together to form the air blowing device 309. An example of an air nozzle, i.e. air blowing head, which could be used is the AIR NOZZLE SILVENT 9002W-S from Silvent AB. However, the air blowing device is not limited to be an air knife or several air nozzles connected together from the company Silvent AB. Any other suitable air blowing device can be used in order to remove dust and loose fibers or other contaminants from the surfaces of the elastic strands.

Figure 7C:
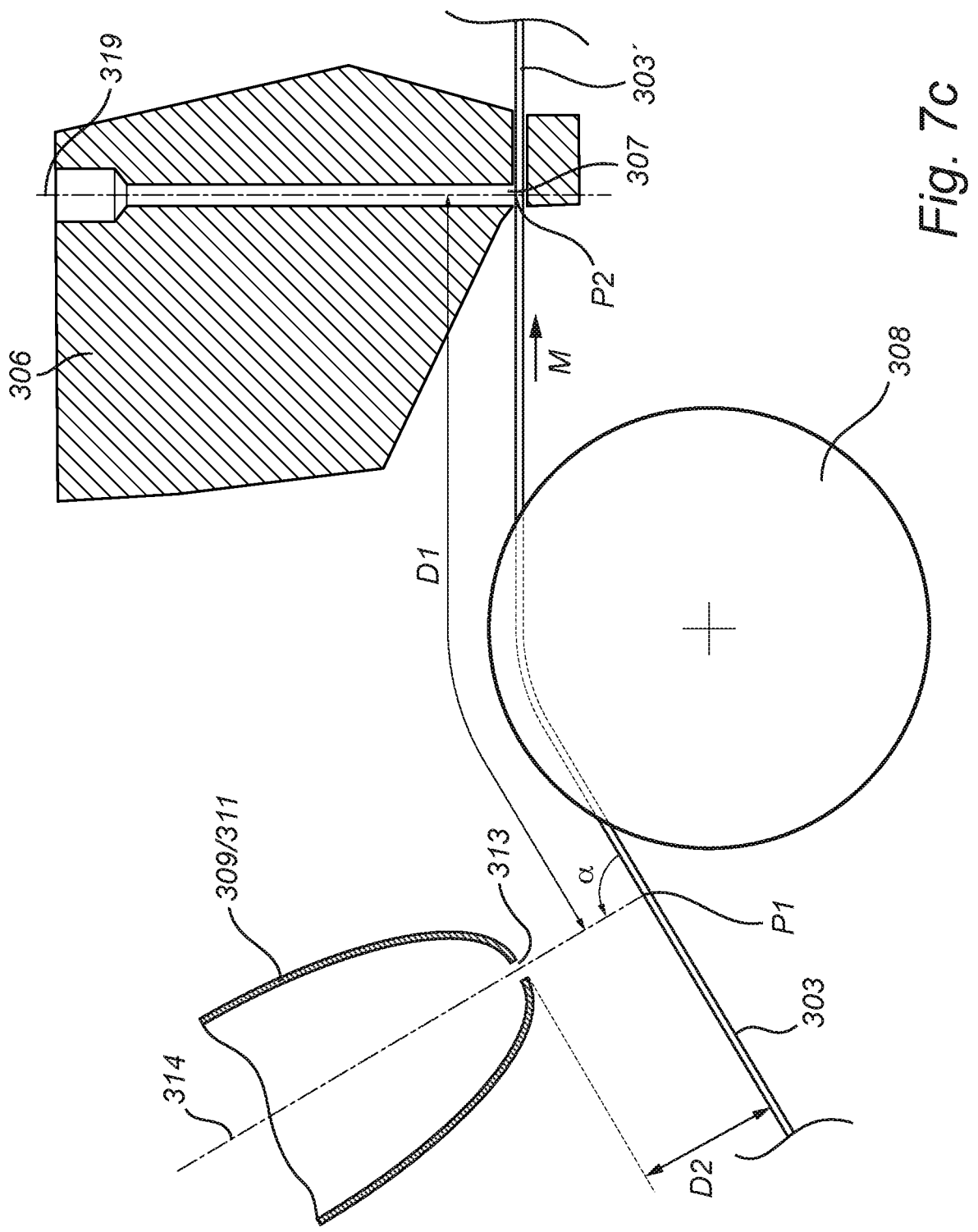

The air blowing device 309 is arranged at a predetermined distance D1 upstream of the nozzle 305 before the liquid adhesive is dispensed onto said elastic strand 303. FIG. 7c shows an enlarged view of the air blowing device 309 arranged at predetermined distance D1 upstream of nozzle 305 before the liquid adhesive is dispensed onto said elastic strand 303 in FIG. 7a. The air blowing device 309 in FIG. 7c is shown in a cross-section view along the machine direction through one of the air discharge passages 313. The air discharge passage 313 comprises a first imaginary centre axis 314 which in its extension intersects with the elastic strand 303 at a first point P1. The nozzle 306 is also shown in a cross-section view along the machine direction in FIG. 7 through one of the liquid discharge passages 307. The liquid discharge passage 307 comprises a second imaginary centre axis 319 which in its extension intersects with the one elastic strand 303 at a second point P2. The predetermined distance D1 is to be measured between said first point P1 and said second point P2 along the elastic strand 303. The predetermined distance D1 is between 150 mm and 900 mm, specifically between 150 mm and 600 mm. Further, said air discharge passage 313 of said air blowing device 309 is arranged above the elastic strand 303 at a predetermined distance D2 from said at least one elastic strand 303. The predetermined distance is to be measured from the air discharge passage 313, i.e. where its opening is, and said first point P1 along said first imaginary centre axis 314. The predetermined distance D2 is between about 30 and about 70 mm. The advantage of having the air discharge passage 313 close to the elastic strand 303 is that less air energy (bar) is needed to blow the dust away. This also reduces the risk of undesired air flow in the surrounding of the air blowing device, which in a worst-case scenario can disturb other parts of the manufacturing line.

The first imaginary centre axis 314 which in its extension intersects with the elastic strand 303 at the first point P1 is arranged at an angle α. The angle is 90° (approximately) relative to the elastic strand (303, 303"). It may however be in an angle which is between about 50° and about 130°, for example from about 70° to about 110°. This way the air 310 (Shown in FIG. 7a) is blown at an angle onto the elastic strand 303. How this can be done is exemplified in FIGS. 7d and 7e, which both are similar to FIG. 7c hence only the differences will be described.

Figure 7D:
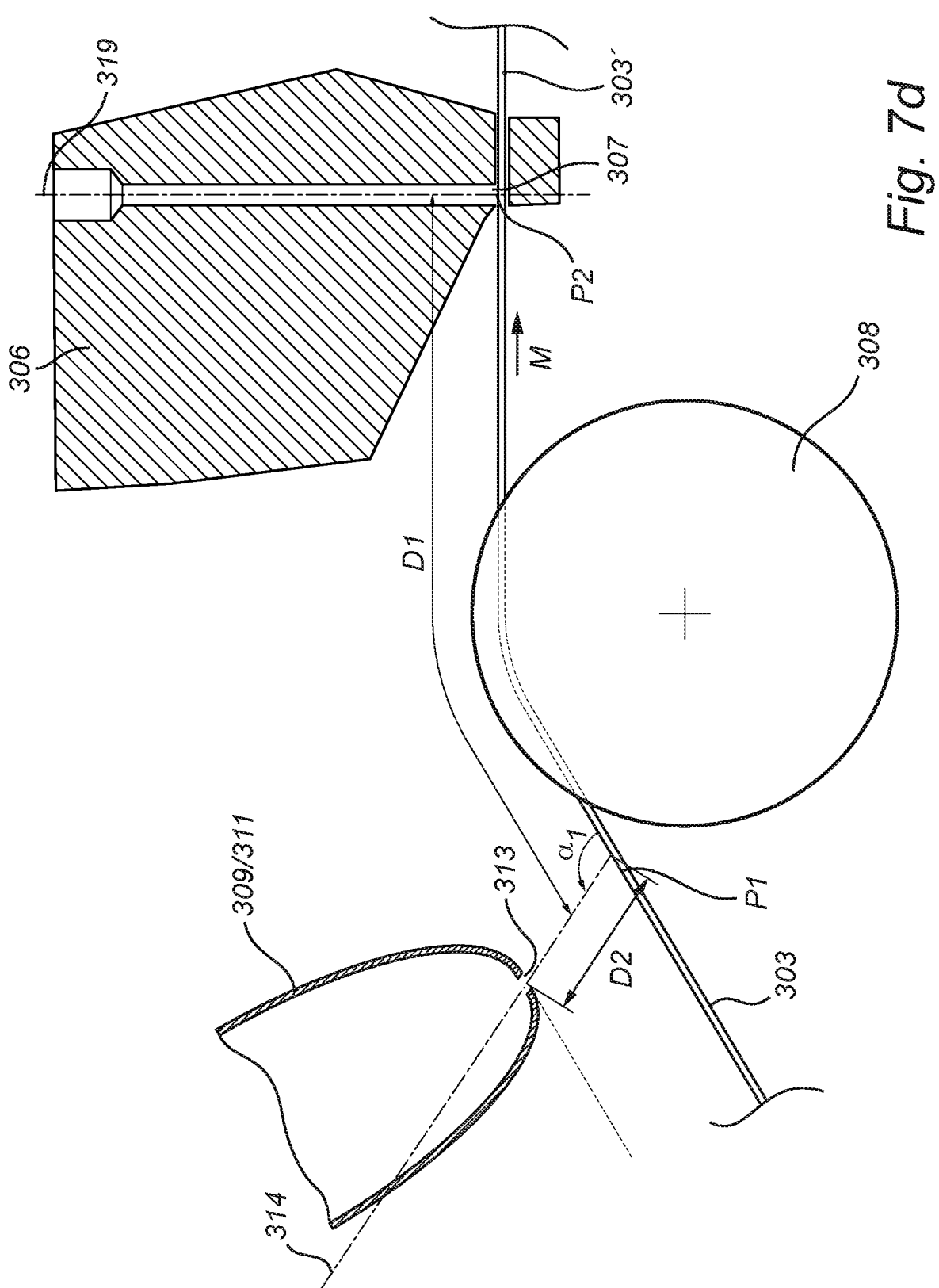
FIG. 7d shows a similar figure as in FIG. 7c but with a second embodiment of the air blowing device.

The FIG. 7d is similar to FIG. 7c except that the air discharge passage 313 is arrange in another position, i.e. another direction, in the air blowing device 309 such that the first imaginary centre axis 314 of the air discharge passage 313 intersects in its extension the elastic strand 303 at the first point (P1) at a second angle α1 which is larger than 90°.

Figure 7E:
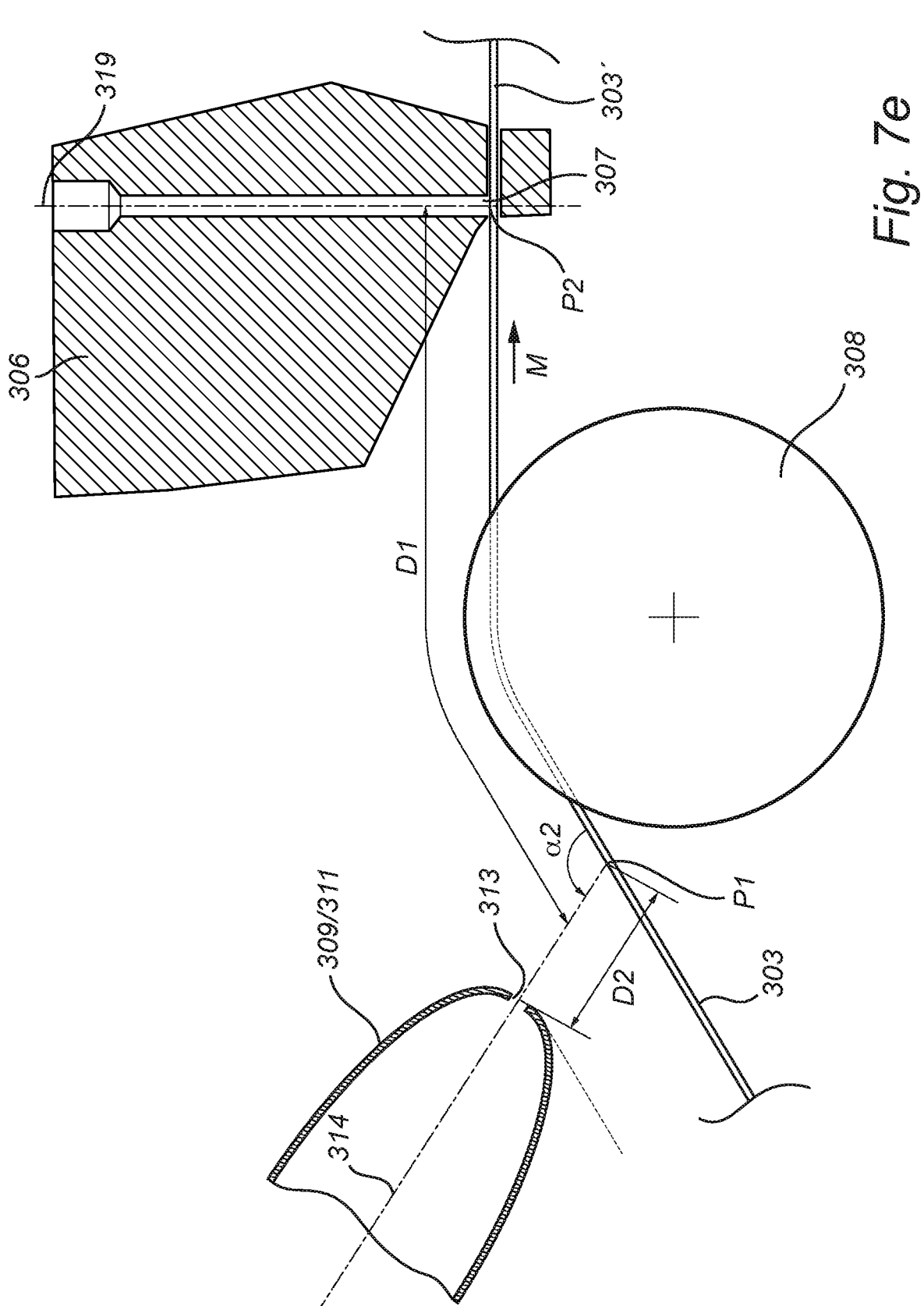
FIG. 7e shows a similar figure as in FIG. 7c but with the air blowing device in FIG. 7c arranged in a different angle to an elastic strand.

The FIG. 7e is similar to FIG. 7c except that the air blowing device 309 is mounted such that the first imaginary centre axis 314 of the air discharge passage 313 intersects in its extension the elastic strand 303 at the first point (P1) at a second angle α2 which is larger than 90°. In both FIGS. 7d and 7e the air discharge passage 313 is also arranged above the elastic strand 303 at a predetermined distance D2 from said at least one elastic strand 303.

The predetermined distance is to be measured from the air discharge passage 313, i.e. where its opening is, and said first point P1 along said first imaginary centre axis 314.

Both variants shown in FIGS. 7d and 7e blows air in a direction towards the nozzle 306, however they may also be so designed that they blow air in a direction which is away from the nozzle 306.

As an alternative to a second continuous sheet in FIGS. 7a and 7b the laminate can be formed by folding the first continuous sheet to form a first layer fold, and directly joining the first continuous sheet and the first layer fold, wherein the first layer fold overlaps said at least one elastic strand. This is shown in FIG. 8.

FIG. 8 shows a similar apparatus to the apparatus in FIGS. 7a and 7b. hence only the differences will be described. In FIG. 8 an elastic laminate 304" comprising two sets of elastic strands 303" is manufactured. Each set comprising three elastic strands. However, more or fewer elastic strands can be provided in the elastic sets. The two sets of elastic strands 303" are attached to one continuous sheet 301. Each set of elastic strands 303" are arranged at respective longitudinal edges 320 of the continuous sheet 301. One air blowing device 309 is provided comprising two air blowing heads 311 connected together in a cross-machine direction with is a direction perpendicular to the machine direction. However, the number air blowing heads is not limited to two or six as shown in FIG. 7a. The number may be higher or lower.

After the elastic strands have been provided with adhesive by the two nozzles 306 the respective longitudinal edges 320 are folded by a folding device (not shown) to form respective layer folds 321 and joining the first continuous sheet 301 and the respective layer fold 321, wherein the layer folds 221 overlaps the respective sets of elastic strand 303" which has been covered by adhesive.

A joining device (not shown) can be arranged after the folding device. The joining device may comprise of two compression rolls with the elastic laminate 304" passing between those compression rolls which is effective to compress the elastic laminate 304", especially at the location of the folds.

The elastic laminate 304" may be used to form a variant of the third sheet 46 of web material or the fourth sheet 49 of web material 49 in FIG. 3 which in a later stage is cut into individual pieces 52 after the absorption body 17 has be arranged between the third sheet 46 of web material and the fourth sheet 49 of web material 49. However, in the variant shown in FIG. 8 an absorption body could be arranged on the laminate 304" and thereafter a second continuous sheet such that the absorption body is laminated between the laminate 304" and the second continuous sheet before it is cut into individual pieces (not shown).

FIG. 9 shows a similar apparatus to the apparatus in FIG. 8. Hence only the differences will be described. In FIG. 9 an elastic laminate 304''' comprising one sets of elastic strands 303" is manufactured. The set comprising three elastic strands 303". However, more or less elastic strands can be provided in the laminate. The elastic strands 303" are attached to one continuous sheet 301. The elastic strands 303" are arranged at one of the two longitudinal edges 320 of the continuous sheet 301. One air blowing device 309 is provided comprising one air blowing head 311 adapted to blow air on the elastic strands 303" in order to remove dust and loose fibres and/or other contaminants.

The elastic strands are coated with adhesive by one nozzle 306. After adhesive has been distributed to the elastic strands 303" the longitudinal edge 320, where the set of elastics strands is arranged, is being folded by a folding device (not shown) to form a layer fold 321 and joining the first continuous sheet 301 and the layer fold 321, wherein the layer fold 221 overlaps the elastic strands 303".

A joining device (not shown) can be arranged after the folding device. The joining device may comprise two compression rolls which the elastic laminate pass between and which compress the elastic laminate, especially where the fold is located. The elastic laminate 304''' may for example be used as a standing gather, which for example is described in FIG. 5

Other products where the elastic laminates described above can be used may for example be a disposable absorbent pad which can be placed in a wearer's underwear. The disposable absorbent pad can be provided with leg elastics or standing gathers in a similar way as the three kind of diapers described herein. Hence, such a disposable absorbent pad will not be further described.

The apparatus and the method described to make an elastic laminate may be part of a larger apparatus which manufactures an absorbent article. Alternatively, it may be a separate apparatus which manufactures a laminate which later on is supplied into another apparatus to manufacture the absorbent article.

The disclosure also covers all conceivable combinations of the described aspects, variants, alternatives and example embodiments of the disclosure.

Furthermore, the disclosure is not limited to the aforesaid aspects or examples, but is naturally applicable to other aspects and example embodiments within the scope of the following claims.

Reference signs mentioned in the claims should not be seen as limiting the extent of the matter protected by the claims, and their sole function is to make claims easier to understand.

The invention claimed is:

1. A method of manufacturing an elastic laminate for a disposable absorbent hygiene product, said elastic laminate comprising at least a first continuous sheet and at least one elastic strand, said method comprising:

advancing said first continuous sheet having a first surface in a machine direction (M), and defining a width in a cross-machine direction;

advancing said at least one elastic strand in the machine direction (M) in a stretched state;

dispensing a liquid adhesive onto said at least one elastic strand from a nozzle comprising at least one liquid discharge passage; and blowing air onto said at least one elastic strand from an air blowing device, said air blowing device being arranged at a predetermined distance (D1) upstream from said nozzle before said liquid adhesive is dispensed onto said at least one elastic strand in order to blow off dust, loose fibers or other contaminants, wherein said air blowing device is a separate device from said nozzle.

2. The method according to claim 1, said method comprising joining said at least one elastic strand to said first surface of said first continuous sheet after said liquid adhesive is dispensed from said liquid discharge passage onto said elastic strand.

3. The method according to claim 1, wherein said air blowing device comprises at least one air discharge passage for blowing said air onto said at least one elastic strand via said air discharge passage, said at least one air discharge passage comprises a first imaginary centre axis which in its extension intersects with said at least one elastic strand at a first point (P1) and said at least one liquid discharge passage of said nozzle comprises a second imaginary centre axis which in its extension intersects with said at least one elastic strand at a second point (P2); and said predetermined distance (D1) is between said first point (P1) and said second point (P2) along said elastic strand and said predetermined distance (D1) is between 150 mm and 900 mm.

4. The method according to claim 1, wherein said method further comprises guiding the at least one elastic strand to said nozzle with an elastic strand guide and said elastic strand guide is arranged between said nozzle and said air blowing device.

5. The method according to claim 4, wherein said elastic strand guide is arranged closer to said air blowing device than to said nozzle.

6. The method according to claim 4, wherein said air blowing device blows air onto said at least one elastic strand guide and onto said elastic strand.

7. The method according to claim 1, wherein said air blowing device blows cold air onto said at least one elastic strand.

8. The method according to claim 1, wherein said air blowing device blows air with an air pressure in the range of 0.5-1.5 bar.

9. The method according to claim 1, wherein said air blowing device comprises at least one air discharge passage for blowing said air onto said at least one elastic strand via said at least one air discharge passage and said at least one air discharge passage is arranged above or under said at least one elastic strand at a predetermined distance (D2) in order to blow air onto said at least one elastic strand.

10. The method according to claim 9, wherein said predetermined distance (D2) between said at least one air discharge passage and said at least one elastic strand is in the range of 30-70 mm.

11. The method according to claim 1, wherein said air blowing device comprises at least one air discharge passage for blowing said air onto said at least one elastic strand via said at least one air discharge passage, said at least one air discharge passage comprises a first imaginary centre axis which in its extension intersects with said at least one elastic strand at a first point (P1), said first imaginary centre axis is in an angle ($\alpha$, $\alpha1$, $\alpha2$) to said at least one elastic strand and said angle ($\alpha$, $\alpha1$, $\alpha2$) is in the range of between about 50°-130°.

12. The method according to claim 1, wherein said method further comprises folding the first continuous sheet to form a first layer fold, and joining the first continuous sheet and the first layer fold, wherein the first layer fold overlaps said at least one elastic strand.

13. The method according to claim 1, wherein said method further comprises advancing a second continuous sheet having a first surface in the machine direction (M), and defining a width in a cross-machine direction, joining said at least one elastic strand between said first surface of said first continuous sheet and said first surface of said second continuous sheet after said liquid adhesive is dispensed from said liquid discharge passage onto said at least one elastic strand.

14. An apparatus for manufacturing an elastic laminate for a disposable absorbent hygiene product, said elastic laminate comprising at least a first continuous sheet and at least one elastic strand, said apparatus comprising:

a first feeding device configured to continuously advancing said first continuous sheet having a first surface in a machine direction (M), and defining a width in a cross-machine direction;

a second feeding device configured to continuously advancing at least one elastic strand in the machine direction (M) in a stretched state;

a nozzle having at least one liquid discharge passage to dispense a liquid adhesive onto said at least one elastic strand; and an air blowing device arranged at a predetermined distance (D1) upstream from said nozzle so that said air blowing device blows air onto said at least one elastic strand before said liquid adhesive is dispensed onto said at least one elastic strand, wherein said air blowing device is a separate device from said nozzle.

15. An apparatus according to claim 14, said method further comprising a joining device configured to join said at least one elastic strand to said first surface of said first continuous sheet after said liquid adhesive is dispensed from said liquid discharge passage onto said at least one elastic strand.

16. An apparatus according to claim 14, wherein said air blowing device comprises at least one air discharge passage for blowing said air onto said at least one elastic strand via said at least one air discharge passage, said at least one air discharge passage comprises a first imaginary centre axis which in its extension intersects with said at least one elastic strand at a first point (P1) and said at least one liquid discharge passage of said nozzle comprises a second imaginary centre axis which in its extension intersects with said at least one elastic strand at a second point (P2); and said predetermined distance (D1) is between said first point (P1) and said second point (P2) along said elastic strand and said predetermined distance (D1) is between 150 mm and 900 mm.

17. An apparatus according to claim 14, wherein said apparatus further comprises an elastic strand guide arranged to guide said at least one elastic strand to said nozzle and said elastic strand guide is arranged between said nozzle and said air blowing device.

18. An apparatus according to claim 17, wherein said elastic strand guide is arranged closer to said air blowing device than to said nozzle.

19. An apparatus according to claim 17, wherein said air blowing device blows air onto said elastic strand guide and onto said at least one elastic strand.

20. An apparatus according to claim 14, wherein said air blowing device blows cold air onto said at least one elastic strand.

21. An apparatus according to claim 14, wherein said air blowing device blows air with an air pressure in the range of 0.5-1.5 bar.

22. An apparatus according to claim 14, wherein said air blowing device comprises at least one an air discharge passage for blowing said air onto said at least one elastic strand via said at least one air discharge passage and said at least one air discharge passage is arranged above or under said at least one elastic strand at a predetermined distance (D2).

23. An apparatus according to claim 22, wherein said predetermined distance (D2) between said at least one air discharge passage and said at least one elastic strand is in the range of 30-70 mm.

24. An apparatus according to claim 14, wherein said air blowing device comprises at least one air discharge passage for blowing said air onto said at least one elastic strand via said at least one air discharge passage, said at least one air discharge passage comprises a first imaginary centre axis which in its extension intersects with said at least one elastic strand at a first point (P1), said first imaginary centre axis is in an angle (α, α1, α2) to said at least one elastic strand and said angle (α, α1, α2) is in the range between about 50°-130°.

25. An apparatus according to claim 14, wherein said air blowing device comprises at least one air discharge passage, and each of said at least one air discharge passages blows air onto a respective elastic strand.

26. An apparatus according to claim 14, wherein said apparatus further comprises a folding device folding the first continuous sheet to form a first layer fold, and directly joining the continuous sheet and the first layer fold, wherein the first layer fold overlaps said at least one elastic strand.

27. An apparatus according to claim 14, wherein said apparatus further comprises a third feeding device configured to continuously advancing a second continuous sheet having a first surface in a machine direction (M), and defining a width in a cross-machine direction, and a joining device to join said at least one elastic strand between said first surface of said first continuous sheet and said first surface of said second continuous sheet after said liquid adhesive is dispensed from said liquid discharge passage onto said elastic strand.

* * * * *